(12) United States Patent
Engel et al.

(10) Patent No.: US 9,809,835 B2
(45) Date of Patent: Nov. 7, 2017

(54) QUANTITATIVE CONTROL OF SIALYLATION

(71) Applicant: Roche Diagnostics Operations, Inc., Indianapolis, IN (US)

(72) Inventors: Alfred Engel, Weilheim (DE); Michael Greif, Penzberg (DE); Christine Jung, Iffeldorf (DE); Sebastian Malik, Antdorf (DE); Rainer Mueller, Penzberg (DE); Harald Sobek, Biberach (DE); Bernhard Suppmann, Weilheim (DE); Marco Thomann, Penzberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 239 days.

(21) Appl. No.: 14/950,443

(22) Filed: Nov. 24, 2015

(65) Prior Publication Data

US 2016/0076068 A1    Mar. 17, 2016

Related U.S. Application Data

(63) Continuation of application No. PCT/EP2014/060101, filed on May 16, 2014.

(30) Foreign Application Priority Data

May 29, 2013 (EP) .................................. 13169714
Jul. 5, 2013 (EP) .................................. 13175390

(51) Int. Cl.
| | | |
|---|---|---|
| C12P 19/44 | (2006.01) | |
| C12P 21/00 | (2006.01) | |
| C12N 9/10 | (2006.01) | |
| C12P 19/02 | (2006.01) | |
| C12P 19/18 | (2006.01) | |

(52) U.S. Cl.
CPC ............ *C12P 19/18* (2013.01); *C12N 9/1081* (2013.01); *C12P 19/02* (2013.01); *C12P 19/44* (2013.01); *C12P 21/005* (2013.01)

(58) Field of Classification Search
None
See application file for complete search history.

(56) References Cited

U.S. PATENT DOCUMENTS

| | | |
|---|---|---|
| 5,032,519 A | 7/1991 | Paulson et al. |
| 2013/0071390 A1 | 3/2013 | Stadheim et al. |

FOREIGN PATENT DOCUMENTS

| | | |
|---|---|---|
| JP | 2008-278761 A | 11/2008 |
| WO | 2005023872 A1 | 3/2005 |
| WO | 2005/078013 A1 | 8/2005 |
| WO | 2007135194 A2 | 11/2007 |
| WO | 2012/113863 A1 | 8/2012 |

OTHER PUBLICATIONS

International Search Report dated Aug. 11, 2014 in Application No. PCT/EP2014/060101, 6 pages.
Anumula, Kalyan Rao, Quantitative glycan profiling of normal human plasma derived immunoglobulin and its fragments Fab and Fc, Journal of Immunological Methods, 2012, pp. 167-176, vol. 382.
Chung, Seung-Wook et al., Galactosylation and sialylation of terminal glycan residues of human immunoglobulin G using bacterial glycosyltransferases with in situ regeneration of sugar-nucleotides, Enzyme and Microbial Technology, 2006, pp. 60-66, vol. 39, No. 1.
Donadio, Sandrine et al., Recognition of cell surface acceptors by two human α-2,6-sialyltransferases produced in CHO cells, Biochimie, 2003, pp. 311-321, vol. 85.
Hamako, Jiharu et al., Comparative Studies of Asparagine-Linked Sugar Chains of Immunoglobulin G from Eleven Mammalian Species, Comparative Biochemistry and Physiology Part B, 1993, pp. 949-954, vol. 106B, No. 4.
Nikonova, E. Yu et al., Specificity of human trans-sialidase as probed with gangliosides, Bioorganic & Medicinal Chemistry Letters, 2004, pp. 5161-5164, vol. 14.
Altschul, Stephen F. et al., Gapped BLAST and PSI-BLAST: a new generation of protein database search programs, Nucleic Acids Research, 1997, pp. 3389-3402, vol. 25, No. 17.
Anderson, J. Christopher et al., An expanded genetic code with a functional quadruplet codon, Proceedings of the National Academy of Sciences USA, 2004, pp. 7566-7571, vol. 101, No. 20.
Bacher, Jamie M. and Ellington, Andrew D., Selection and Characterization of *Escherichia coli* Variants Capable of Growth on an Otherwise Toxic Tryptophan Analogue, Journal of Bacteriology, 2001, pp. 5414-5425, vol. 183, No. 18.
Backliwal, Gaurav et al., Rational vector design and multi-pathway modulation of HEK 293E cells yield recombinant antibody tiers exceeding 1 g/l by transient transfaction under serum-free conditions, Nucleic Acids Research, 2008, e96, 7 pages, vol. 36, No. 15.
Barb, Adam W, et al., Branch-Specific Sialylation of IgG-Fc Glycans by ST6Gal-I, Biochemistry, 2009, pp. 9705-9707, vol. 48.
Bork, Kaya et al., Increasing the Sialylation of Therapeutic Glycoproteins: The Potential of the Sialic Acid Biosynthetic Pathway, Journal of Pharmaceutical Sciences, 2009, pp. 3499-3508, vol. 98, No. 10.

(Continued)

*Primary Examiner* — Suzanne M Noakes
*Assistant Examiner* — Jae W Lee
(74) *Attorney, Agent, or Firm* — Roche Diagnostics Operations, Inc.

(57) ABSTRACT

The present disclosure is directed to the use of certain glycosyltransferase variants having N-terminal truncation deletions. Contrary to previous findings certain truncations were found to exhibit sialidase enzymatic activity, particularly a variant of human sialyltransferase (hST6Gal-I) with a truncation deletion involving the first 89 N-terminal amino acids of the respective wild-type polypeptide. A fundamental finding documented in the present disclosure is that there exists a variant of this enzyme which is capable of catalyzing transfer of a glycosyl moiety as well as hydrolysis thereof. Thus, disclosed is a specific exemplary variant of mammalian glycosyltransferase, nucleic acids encoding the same, methods and means for recombinantly producing the variant of mammalian glycosyltransferase and use thereof, particularly for sialylating in a quantitatively controlled manner terminal acceptor groups of glycan moieties being part of glycoproteins such as immunoglobulins.

8 Claims, 6 Drawing Sheets

(56) References Cited

OTHER PUBLICATIONS

Brossmer, Reinhard and Gross, Hans Jürgen, [12] Fluorescent and Photoactivatable Sialic Acids, Methods in Enzymology, 1994, pp. 177-183, vol. 247.

Budisa, Nediljko et al., Proteins with β-(thienophrrolyl)alanines as alternative chromophores and pharmaceutically active amino acids, Protein Science, 2001, pp. 1281-1292, vol. 10.

Chen, Chun and Colley, Karen J., Minimal structural and glycosylation requirements for ST6Gal I activity and trafficking, Glycobiology, 2000, pp. 531-583, vol. 10, No. 5.

Chin, Jason W. et al., An Expanded Eukaryotic Genetic Code, Science, 2003, pp. 964-967, vol. 301.

Dall'Olio, Fabio, The sialyl-α2, 6-lactosaminyl-structure: Biosynthesis and functional role, Glycoconjugate Journal, 2000, pp. 669-676, vol. 17.

Engel, Alfred M. et al, Rec. ST6Gal-I variants to control enzymatic activity in processes of in vitro glycoengineering, BMC Proceedings, 2013, pp. P110-P111, vol. 7 (Supplement 6).

Hamano-Takaku, Fumie et al., A Mutant *Escherichia coli* Tyrosyl-tRNA Synthetase Utilizes the Unnatural Amino Acid Azatyrosine More Efficiently than Tyrosine, The Journal of Biological Chemistry, 2000, pp. 40324-40328, vol. 275, No. 51.

Hidari, Kazuya I.P.J. et al., Purification and characterization of a soluble recombinant human ST6Gal I functionally expressed in *Escherichia coli*, Glycoconjugate Journal, 2005, pp. 1-11, vol. 22.

Ibba, Michael and Söll, Dieter, Genetic Code: Introducing Pyrrolysine, Current Biology, 2002, pp. R464-R466, vol. 12.

Ikeda, Yutaka et al., Synthesis of a novel histidine analogue and its efficient incorporation into a protein in vivo, Protein Engineering, 2003, pp. 699-706, vol. 16, No. 9.

James, D. Andrew et al., Kinetic characterization of ribonuclease S mutants containing photoisomerizable phenylazophenylalanine residues, Protein Engineering, 2001, pp. 983-991, vol. 14, No. 12.

Kilàr, Ference and Hjertén, Stellan, Separation of the Human Transferrin Isoforms by Carrier-Free High-Performance Zone Electrophoresis and Isoelectric Focusing, Journal of Chromatography, 1989, pp. 351-357, vol. 480.

Kitazume-Kawaguchi, Shinobu et al., The relationship between ST6Gal I Golgi retention and its cleavage-secretion, Glycobiology, 1999, pp. 1397-1406, vol. 9, No. 12.

Köhrer, Caroline et al., Import of amber and ochre suppressor tRNAs into mammalian cells: A general approach to site-specific insertion of amino acid analogues into proteins, Proceedings of the National Academy of Sciences USA, 2001, pp. 14310-14315, vol. 98, No. 25.

Legaigneur, Patrick et al., Exploring the Acceptor Substrate Recognition of the Human β-Galactoside α2,6-Sialyltransferase, The Journal of Biological Chemistry, 2000, pp. 21608-21617, vol. 276, No. 24.

Lund, J. et al., Control of IgG/Fc Glycosylation: A Comparison of Oligosaccharides from Chimeric Human/Mouse and Mouse Subclass Immunoglobulin Gs, Molecular Immunology, 1993, pp. 741-748, vol. 30 No. 8.

Malissard, M. et al., Expression of Functional Soluble Forms of Human β-1,4-Galactosyltransferase I, α-2,6-Sialyltransferase, and a α-1,3-Fucosyltransferase VI in the Methylotrophic Yeast Pichia pastoris, Biochemical and Biophysical Research Communications, 2000, pp. 169-173, vol. 267.

Nakamura, Mitsuru et al., CMP-NeuAc:Galβ1→4GlcNAc α2→6sialyltransferase catalyzes NeuAc transfer to glycoplipids, Journal of Lipid Research, 1997, pp. 1795-1806, vol. 38.

Nielsen, Peter E. et al., Sequence-Selective Recognition of DNA by Strand Displacement with a Thymine-Substituted Polyamide, Science, 1991, pp. 1497-1500, vol. 254.

Ogata, Makoto et al., Synthesis of sialoglycopolypeptide for potentially blocking influenza virus infection using a rat α2,6-sialyltransferase expressed in BmNPV bacmid-injected silkworm larvae, BMC Biotechnology, 2009, 54, 13 pages, vol. 9.

Patel, Ronak Y. and Balaji, Petery V., Identification of linkage-specific sequence motifs in sialyltransferases, Glycobiology, 2006, pp. 108-116, vol. 16, No. 2.

Scudder, Peter R. and Chantler, Eric N, Glycosyltransferases of the Human Cervical Epithelium II. Characterization of a CMP-N-Acetylneuraminate: Galactosyl-Glycoprotein Sialyltransferase, Biochimica et Biophysics Acta, 1981, pp. 136-141, vol. 660.

Stadtman, Thressa C., Selenocysteine, Annual Reviews of Biochemistry, 1996, pp. 83-100, vol. 65.

Sticher, Udo et al., Purification and characterization of α(2-6)-sialyltransferase from human liver, Glycoconjugate Journal, 1991, pp. 45-54, vol. 8.

Zhang, Zhiwen et al., Selective incorporation of 5-hydroxytryptophan into proteins in mammalian cells, Proceedings of the National Academy of Sciences USA, 2004, pp. 8882-8887, vol. 101, No. 24.

QUANTITATIVE CONTROL OF SIALYLATION

CROSS-REFERENCE TO RELATED APPLICATIONS

This application is a continuation of International Patent Application No. PCT/EP2014/060101 filed May 16, 2014, which claims priority to European Patent Application No. 13169714.6 filed May 29, 2013, and European Patent Application No. 13175390.7 filed Jul. 5, 2013, the disclosures of which are hereby incorporated by reference in their entirety.

FIELD

The present disclosure is directed to the use of certain glycosyltransferase variants having N-terminal truncation deletions. Contrary to previous findings certain truncations were found to exhibit sialidase enzymatic activity, particularly a variant of human β-galactoside-α-2,6-sialyltransferase I (hST6Gal-I) with a truncation deletion involving the first 89 N-terminal amino acids of the respective wild-type polypeptide. A fundamental finding documented in the present disclosure is that there exists a variant of this enzyme which is capable of catalyzing transfer of a glycosyl moiety as well as hydrolysis thereof. Thus, disclosed is a specific exemplary variant of mammalian glycosyltransferase, nucleic acids encoding the same, methods and means for recombinantly producing the variant of mammalian glycosyltransferase and use thereof, particularly for sialylating in a quantitatively controlled manner terminal acceptor groups of glycan moieties being part of glycoproteins such as immunoglobulins.

BACKGROUND

Transferases (EC 2) catalyze transfer of a functional group from one substance to another. Glycosyltransferases, a superfamily of enzymes, are involved in synthesizing the carbohydrate portions of glycoproteins, glycolipids and glycosaminoglycans. Specific glycosyltransferases synthesize oligosaccharides by the sequential transfer of the monosaccharide moiety of an activated sugar donor to an acceptor molecule. Hence, a "glycosyltransferase" catalyzes the transfer of a sugar moiety from its nucleotide donor to an acceptor moiety of a polypeptide, lipid, glycoprotein or glycolipid. This process is also known as "glycosylation". A carbohydrate portion which is structural part of e.g. a glycoprotein is also refered to as "glycan". Glycans constitute the most prevalent of all known post-translational protein modifications. Glycans are involved in a wide array of biological recognition processes as diverse as adhesion, immune response, neural cell migration and axonal extension. As structural part of glycoproteins glycans also have a role in protein folding and the support of protein stability and biological activity.

In glycosyltransferase catalysis, the monosaccharide units glucose (Glc), galactose (Gal), N-acetylglucosamine (GlcNAc), N-acetylgalactosamine (GalNAc), glucuronic acid (GlcUA), galacturonic acid (GalUA) and xylose are activated as uridine diphosphate (UDP)-α-D derivatives; arabinose is activated as a UDP-β-L derivative; mannose (Man) and fucose are activated as GDP-a-D and GDP-β-L derivatives, respectively; and sialic acid (=Neu5Ac; =SA) is activated as a CMP derivative of β-D-Neu5Ac.

Many different glycosyltransferases contribute to the synthesis of glycans. The structural diversity of carbohydrate portions of glycoproteins is particularly large and is determined by complex biosynthetic pathways. In eukaryotes the biosynthesis of the glycan-part of glycoproteins takes place in the lumen of the endoplasmatic reticulum ("ER") and the Golgi apparatus. A single (branched or linear) carbohydrate chain of a glycoprotein is typically a N- or an O-linked glycan. During post-translational processing, carbohydrates are typically connected to the polypeptide via asparagine ("N-linked glycosylation"), or via serine or threonine ("O-linked glycosylation"). Synthesis of a glycan, no matter whether N- or O-linked (="N-/O-linked") is effected by the activity of several different membrane-anchored glycosyltransferases. A glycoprotein may comprise one or more glycan-connected amino acids (="glycosylation sites"). A specific glycan structure may be linear or branched. Branching is a notable feature of carbohydrates which is in contrast to the linear nature typical for DNA, RNA, and polypeptides. Combined with the large heterogeneity of their basic building blocks, the monosaccharides, glycan structures exhibit high diversity. Furthermore, in members of a particular glycoprotein species the structure of a glycan attached to a particular glycosylation site may vary, thus resulting in microheterogeneity of the respective glycoprotein species, i.e. in a species sharing the same amino acid sequence of the poypeptide portion.

A sialyltransferase (="ST") is a glycosyltransferase that catalyzes transfer of a sialic acid (=5-N-acetylneuramic acid=Neu5Ac=NANA) residue from a donor compound to (i) a terminal monosaccharide acceptor group of a glycolipid or a ganglioside, or (ii) to a terminal monosaccharide acceptor group of an N-/O-linked glycan of a glycoprotein. For mammalian sialyltransferases including human ST species there is a common donor compound which is cytidine-5'-monophospho-N-acetylneuraminic acid (=CMP-Neu5Ac=CMP-NANA). Transfer of a sialic acid residue is also referred to as "sialylating" and "sialylation".

In the glycan structure of a sialylated glycoprotein the (one or more) sialyl moiety (moieties) is (are) usually found in terminal position of the oligosaccharide. Owing to the terminal, i.e. exposed position, sialic acid can participate in many different biological recognition phenomena and serve in different kinds of biological interactions. In a glycoprotein more than one sialylation site may be present, i.e. a site capable of serving as a substrate for a sialyltransferase and being an acceptor group suitable for the transfer of a sialic acid residue. Such more than one site can in principle be the termini of a plurality of linear glycan portions anchored at different glycosylation sites of the glycoprotein. Additionally, a branched glycan may have a plurality of sites where sialylation can occur.

According to current knowledge, a terminal sialic acid residue can be found (i) α2→3 (α2,3) linked to galactosyl-R, (ii) α→26 (α2,6) linked to galactosyl-R, (iii) α2→6 (α2,6) linked to N-acetylgalactosaminidyl-R, (iv) α2→6 (α2,6) linked to N-acetylglucosaminidyl-R, and (v) α2→8/9 (α2,8/9) linked to sialidyl-R, wherein -R denotes the rest of the acceptor substrate moiety. Hence, a sialyltransferase active in the biosynthesis of sialylconjugates (="sialylation") is generally named and classified according to its respective monosaccharide acceptor substrate and according to the 3, 6 or 8/9 position of the glycosidic bond it catalyzes. Accordingly, in the literature known to the art, e.g. in Patel R Y, et al, Glycobiology 16 (2006) 108-116, reference to eukaryotic sialyltransferases is made such as (i) ST3Gal, (ii) ST6Gal, (iii) ST6GalNAc, or (v) ST8Sia, depending on the hydroxyl position of the acceptor sugar residue to which the Neu5Ac residue is transferred while forming a glycosidic bond. Reference to sialyltransferases in a more generic way can also be made e.g. as ST3, ST6, ST8; thus, "ST6" specifically encompasses the sialyltransferases catalyzing an α2,6 sialylation.

The disaccharide moiety β-D-galactosyl-1,4-N-acetyl-β-D-glucosamine (=Galβ1,4GlcNAc) is a frequent terminal residue of the antennae of N-linked glycans of glycoproteins, but may be also present in O-linked glycans and in glycolipids. The enzyme β-galactoside-α2,6-sialyltransferase (="ST6Gal") is able to catalyze α2,6-sialylation of a terminal Galβ1,4GlcNAc of a glycan or a branch of a glycan (="antenna"). For general aspects thereof, reference is made to the document of DallOlio F. Glycoconjugate Journal 17 (2000) 669-676. In human and in other mammals there appear to be several species of ST6Gal. The present disclosure particularly deals with human β-galactoside-α-2,6-sialyltransferase I (=hST6Gal-I; EC 2.4.99.1 according to IUBMB Enzyme Nomenclature), but is not limited thereto.

The ST6 group of sialyltransferases comprises 2 subgroups, ST6Gal and ST6GalNAc. The activity of ST6Gal enzymes catalyzes transfer of a Neu5Ac residue to the C6 hydroxyl group of a free galactosyl residue being part of terminal Galβ1,4GlcNAc in a glycan or an antenna of a glycan, thereby forming in the glycan a terminal sialic acid residue α2→6 linked to the galactosyl residue of the Galβ1,4GlcNAc moiety. The resulting newly formed terminal moiety in the glycan is Neu5Acα2,6Galβ1,4GlcNAc.

The wild-type polypeptide of human β-galactoside-α-2,6-sialyltransferase I (hST6Gal-I) at the time of filing of the present document was disclosed as "UniProtKB/Swiss-Prot: P15907.1" in the publically accessible NCBI database (www.ncbi.nlm.nih.gov/protein/115445). Further information including coding sequences are provided as hyperlinks compiled within the database entry "Gene ID: 6480" (www.ncbi.nlm.nih.gov/gene/6480).

Mammalian sialyltransferases share with other mammalian Golgi-resident glycosyltransferases a so-called "type II architecture" with (i) a short cytoplasmic N-terminal tail, (ii) a transmembrane fragment followed by (iii) a stem region of variable length and (iv) a C-terminal catalytic domain facing the lumen of the Golgi apparatus (Donadio S. et al. in Biochimie 85 (2003) 311-321). Mammalian sialyltransferases appear to display significant sequence homology in their catalytic domain.

Donadio S. et al. expressed several N-terminally truncated variants of hST6Gal-I in CHO cells and found that N-terminal deletions comprising the first 35, 48, 60 and 89 amino acids yielded mutant enzymes which nevertheless were still active in transferring sialic acid to exogenous acceptors.

Glycosylation is an important posttranslational modification of proteins influencing protein folding, stability and regulation of the biological activity. The sialyl mojety (=sialic acid, 5-N-acetylneuramic acid, Neu5Ac) is usually exposed at the terminal position of N-glycosylation and therefore, a major contributor to biological recognition and ligand function, e.g. IgG featuring terminal sialic acids were shown to induce less inflammatory response and increased serum half-life.

The use of glycosyltransferases for enzymatic synthesis of defined glycan structures is becoming a tool to direct N-glycosylation of therapeutic proteins such as antibodies. Since glycosyltransferases of prokaryotic origin usually do not act on complex glycoprotein structures, sialyltransferases of mammalian origin are preferred. For example, Barb et al. (2009) prepared highly potent sialylated forms of the Fc fragment of immunoglobulin G using isolated human ST6Gal-I. However, the access to recombinant ST6Gal-I for therapeutic applications is still limited due to low expression and/or poor activity in various hosts (*Pichia pastoris, Spodoptera frugiperda* and *E. coli*).

It is known to the art that mammalian glycosyltransferases can be used advantageously for in vitro sialylating a complex target molecule such as a glycoprotein or a glycolipid. However, the opposite reaction (sialidase activity, hydrolytic cleavage of a terminal sialyl residue from a glycan moiety) is typically provided by a neuraminidase. The original finding by the present inventors is, however, that a variant of a sialyltransferase of mammalian origin displays sialidase activity. In fact, a specific variant of human human β-galactoside-α-2,6-sialyltransferase I with an N-terminal truncation can be used for both, (i) sialylation of a target glycoprotein and (ii) hydrolytic cleavage of sialyl residues from the sialylated target glycoprotein. Depending on the control of kinetics of the variant enzyme, sialylation can be controlled quantitatively. That is to say, the present disclosure provides means, methods and conditions allowing to sialylate just one out of the several acceptor sites as opposed to sialylating two or more, or even all acceptor sites of the target molecule.

This paves the way for a number of different approaches, particularly in the field of in vitro glycoengineering of immunoglobulins, and also of other glycosylated target molecules. Here specifically and exemplarily a method is provided resulting in the production of predominantly mono-sialylated or bi-sialylated immunoglobulin G molecules. However, a number of other in vitro sialylation approaches with quantitative sialylation control of the target molecule to be sialylated become feasible and can be deduced from the present disclosure.

In a specific embodiment this document further discloses the high-yield expression of a Δ89 N-terminal truncation variant of human β-galactoside-α-2,6-sialyltransferase I (hST6Gal-I, EC 2.4.99.1; data base entry P15907) by transient gene expression in HEK293 cells with yields up to 100 mg/L featuring a surprisingly distinct sialylation activity.

SUMMARY

In a first aspect there is disclosed the use of N-terminally truncated human β-galactoside-α-2,6-sialyltransferase I having the amino acid sequence of SEQ ID NO:2 for hydrolyzing the α2,6 glycosidic bond in a N-acetylneuraminyl-α2,6-β-D-galactosyl- 1,4-N-acetyl-β-D-glucosamine moiety, the moiety being a terminal structure of a glycan in a sialylated glycoprotein or glycolipid.

In a further aspect there is disclosed a method to hydrolyze the α2,6 glycosidic bond in a N-acetylneuraminyl-α2,6-β-D-galactosyl-1,4-N-acetyl-β-D-glucosamine moiety, the moiety being a terminal structure of a glycan in a sialylated glycoprotein or glycolipid, the method comprising the steps of (a) providing in an aqueous solution a sialylated glycoprotein or glycolipid with a terminal N-acetylneuraminyl-α2,6-β-D-galactosyl-1,4-N-acetyl-β-D-glucosamine moiety in the glycan portion of said glycoprotein; (b) incubating the N-acetylneuraminyl-α2,6-β-D-galactosyl-1,4-N-acetyl-β-D-glucosamine moiety with a N-terminally truncated human β-galactoside-α-2,6-sialyltransferase I having the amino acid sequence of SEQ ID NO:2; thereby hydrolyzing the α2,6 glycosidic bond in the N-acetylneuraminyl-α2,6-β-D-galactosyl-1,4-N-acetyl-β-D-glucosamine moiety.

In a yet a further aspect there is disclosed a method of producing in vitro a sialylated target molecule with a controlled quantity of sialyl residues, the method comprising the steps of (a) providing a glycosylated target molecule in an aqueous solution and under conditions permitting glycosyltransferase enzymatic activity, the target molecule being selected from a glycoprotein and a glycolipid, the target molecule comprising a plurality of antennae, at least two of the antennae each having as terminal structure a β-D-galactosyl-1,4-N-acetyl-β-D-glucosamine moiety with a hydroxyl group at the C6 position in the galactosyl residue; (b) forming one or more terminal antennal N-acetylneuraminyl-α2,6-β-D-galactosyl-1,4-N-acetyl-β-D-glucosamine residue(s) [=α2,6 sialylated terminal antennal residue(s)] by incubating the target molecule of step (a) for a first pre-determined time with N-terminally truncated human β-galactoside-α-2,6-sialyltransferase I having the amino acid sequence of SEQ ID NO:2 and in the presence of cytidine-5'-monophospho-N-acetylneuraminic acid, or a functional equivalent thereof, as donor compound thereby providing a sialylated target molecule; (c) hydrolyzing the α2,6 glycosidic bond in one or more terminal antennal N-acetylneuraminyl-α2,6-β-D-galactosyl-1,4-N-acetyl-β-D-glucosamine residues by incubating the sialylated target molecule of step (b) for a second pre-determined time with the N-terminally truncated human β-galactoside-α-2,6-sialyltransferase I having the amino acid sequence of SEQ ID NO:2; thereby producing in vitro the sialylated target molecule with a controlled quantity of sialyl residues.

In a yet a further aspect there is disclosed a preparation of glycosylated target molecules, the target molecules being immunoglobulin molecules of the IgG class, wherein the amount of bi-sialylated target molecules in the preparation is about 35% to about 90%, the preparation being obtained by a method as disclosed herein.

In a yet a further aspect there is disclosed a preparation of glycosylated target molecules, the target molecules being immunoglobulin molecules of the IgG class, wherein the amount of mono-sialylated target molecules in the preparation is about 60% to about 75%, the preparation being obtained by a method as disclosed herein.

In a yet a further aspect there is disclosed a preparation of glycosylated target molecules, the target molecules being immunoglobulin molecules of the IgG class, wherein the amounts of mono-and bi-sialylated target molecules in the preparation are controlled quantities, the preparation being obtained by a method as disclosed herein.

In a yet a further aspect there is disclosed the use of a preparation of glycosylated immunoglobulin molecules as disclosed herein for preparing a pharmaceutical composition.

DETAILED DESCRIPTION

Figure 1:
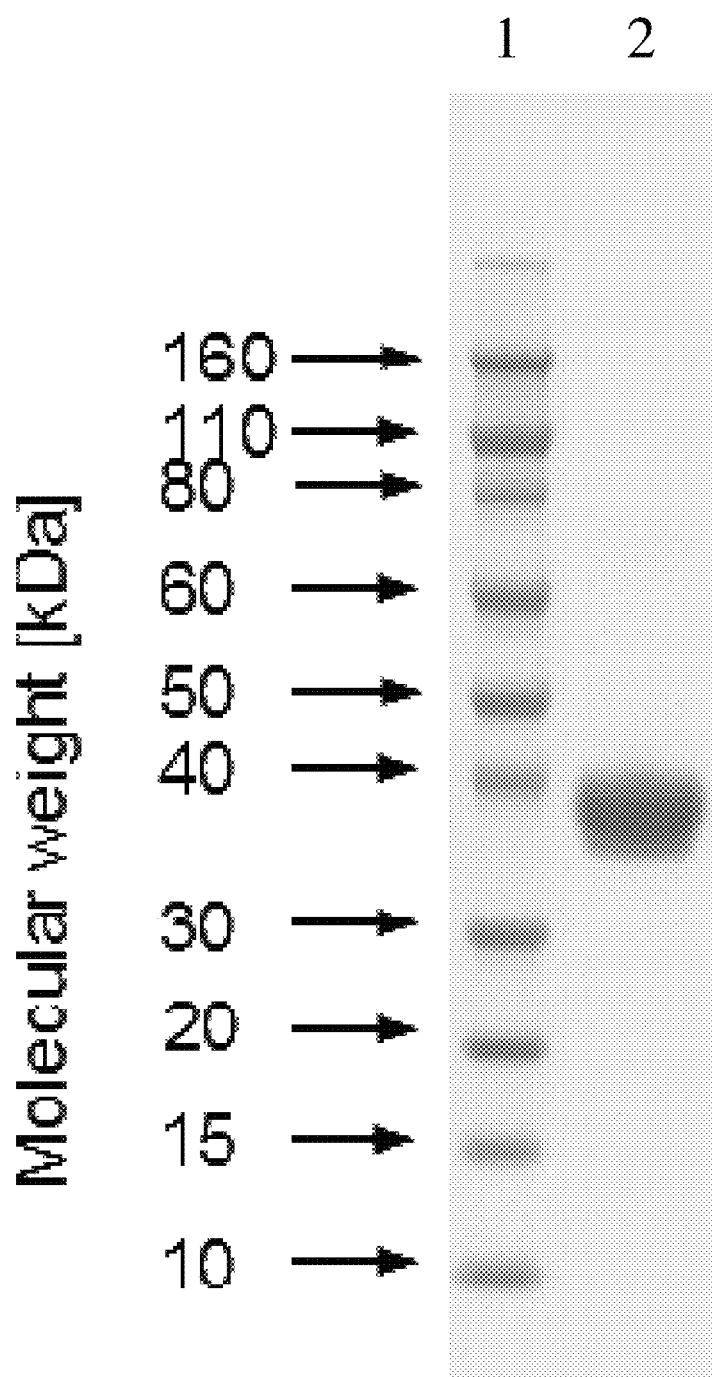
FIG. 1 SDS-PAGE of purified recombinant Δ89 hST6Gal-I. Lane 1: molecular weight marker; lane 2: Purified enzyme, 5 µg were loaded onto the gel.

The terms "a", "an" and "the" generally include plural referents, unless the context clearly indicates otherwise. As used herein, "plurality" is understood to mean more than one. For example, a plurality refers to at least two, three, four, five, or more. Unless specifically stated or obvious from context, as used herein, the term "or" is understood to be inclusive.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

The term "amino acid" generally refers to any monomer unit that can be incorporated into a peptide, polypeptide, or protein. As used herein, the term "amino acid" includes the following twenty natural or genetically encoded alpha-amino acids: alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V). In cases where "X" residues are undefined, these should be defined as "any amino acid." The structures of these twenty natural amino acids are shown in, e.g., Stryer et al., Biochemistry, 5th ed., Freeman and Company (2002). Additional amino acids, such as selenocysteine and pyrrolysine, can also be genetically coded for (Stadtman (1996) "Selenocysteine," Annu Rev Biochem. 65:83-100 and Ibba et al. (2002) "Genetic code: introducing pyrrolysine," Curr Biol. 12(13):R464-R466). The term "amino acid" also includes unnatural amino acids, modified amino acids (e.g., having modified side chains and/or backbones), and amino acid analogs. See, e.g., Zhang et al. (2004) "Selective incorporation of 5-hydroxytryptophan into proteins in mammalian cells," Proc. Natl. Acad. Sci. U.S.A. 101(24):8882-8887, Anderson et al. (2004) "An expanded genetic code with a functional quadruplet codon" Proc. Natl. Acad. Sci. U.S.A. 101(20):7566-7571, Ikeda et al. (2003) "Synthesis of a novel histidine analogue and its efficient incorporation into a protein in vivo," Protein Eng. Des. Sel. 16(9):699-706, Chin et al. (2003) "An Expanded Eukaryotic Genetic Code," Science 301(5635):964-967, James et al. (2001) "Kinetic characterization of ribonuclease S mutants containing photoisomerizable phenylazophenylalanine residues," Protein Eng. Des. Sel. 14(12):983-991, Kohrer et al. (2001) "Import of amber and ochre suppressor tRNAs into mammalian cells: A general approach to site-specific insertion of amino acid analogues into proteins," Proc. Natl. Acad. Sci. U.S.A. 98(25):14310-14315, Bacher et al. (2001) "Selection and Characterization of Escherichia coli Variants Capable of Growth on an Otherwise Toxic Tryptophan Analogue," J. Bacteriol. 183(18):5414-5425, Hamano-Takaku et al. (2000) "A Mutant *Escherichia coli* Tyrosyl-tRNA Synthetase Utilizes the Unnatural Amino Acid Azatyrosine More Efficiently than Tyrosine," J. Biol. Chem. 275(51):40324-40328, and Budisa et al. (2001) "Proteins with { beta}-(thienopyrrolyl)alanines as alternative chromophores and pharmaceutically active amino acids," Protein Sci. 10(7):1281-1292. To further illustrate, an amino acid is typically an organic acid that includes a substituted or unsubstituted amino group, a substituted or unsubstituted carboxy group, and one or more side chains or groups, or analogs of any of these groups. Exemplary side chains include, e.g., thiol, seleno, sulfonyl, alkyl, aryl, acyl, keto, azido, hydroxyl, hydrazine, cyano, halo, hydrazide, alkenyl, alkynl, ether, borate, boronate, phospho, phosphono, phosphine, heterocyclic, enone, imine, aldehyde, ester, thioacid, hydroxylamine, or any combination of these groups. Other representative amino acids include, but are not limited to, amino acids comprising photoactivatable cross-linkers, metal binding amino acids, spin-labeled amino acids, fluorescent amino acids, metal-containing amino acids, amino acids with novel functional groups, amino acids that covalently or noncovalently interact with other molecules, photocaged and/or photoisomerizable amino acids, radioactive amino acids, amino acids comprising biotin or a biotin analog, glycosylated amino acids, other carbohydrate modified amino acids, amino acids comprising polyethylene glycol or polyether, heavy atom substituted amino acids, chemically cleavable and/or photocleavable amino acids, carbon-linked sugar-containing amino acids, redox-active amino acids, amino thioacid containing amino acids, and amino acids comprising one or more toxic moieties.

The term "protein" refers to a polypeptide chain (amino acid sequence) as a product of the ribosomal translation process, wherein the polypeptide chain has undergone post-translational folding processes resulting in three-dimensional protein structure. The term "protein" also encompasses polypeptides with one or more posttranslational modifications such as (but not limited to) glycosylation, phosphorylation, acetylation and ubiquitination.

Any protein as disclosed herein, particularly recombinantly produced protein as disclosed herein, may in a specific embodiment comprise a "protein tag" which is a peptide sequence genetically grafted onto the recombinant protein. A protein tag may comprise a linker sequence with a specific protease claeavage site to facilitate removal of the tag by proteolysis. As a specific embodiment, an "affinity tag" is appended to a target protein so that the target can be purified from its crude biological source using an affinity technique. For example, the source can be a transformed host organism expressing the target protein or a culture supernatant into which the target protein was secreted by the transformed host organism. Specific embodiments of an affinity tag include chitin binding protein (CBP), maltose binding protein (MBP), and glutathione-S-transferase (GST). The poly(His) tag is a widely-used protein tag which facilitates binding to certain metal chelating matrices.

Each of the terms "chimeric protein", "fusion protein" or "fusion polypeptide" equally refers to a protein whose amino acid sequence represents a fusion product of subsequences of the amino acid sequences from at least two distinct proteins. A fusion protein typically is not produced by direct manipulation of amino acid sequences, but, rather, is expressed from a "chimeric" gene that encodes the chimeric amino acid sequence.

The term "recombinant" refers to an amino acid sequence or a nucleotide sequence that has been intentionally modified by recombinant methods. By the term "recombinant nucleic acid" herein is meant a nucleic acid, originally formed in vitro, in general, by the manipulation of a nucleic acid by endonucleases, in a form not normally found in nature. Thus an isolated, mutant DNA polymerase nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. A "recombinant protein" or "recombinantly produced protein" is a protein made using recombinant techniques, i.e., through the expression of a recombinant nucleic acid as depicted above.

A nucleic acid is "operably linked" when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation.

The term "host cell" refers to both single-cellular prokaryote and eukaryote organisms (e.g., mammalian cells, insect cells, bacteria, yeast, and actinomycetes) and single cells from higher order plants or animals when being grown in cell culture.

The term "vector" refers to a piece of DNA, typically double-stranded, which may have inserted into it a piece of foreign DNA. The vector or may be, for example, of plasmid origin. Vectors contain "replicon" polynucleotide sequences that facilitate the autonomous replication of the vector in a host cell. Foreign DNA is defined as heterologous DNA, which is DNA not naturally found in the host cell, which, for example, replicates the vector molecule, encodes a selectable or screenable marker, or encodes a transgene. The vector is used to transport the foreign or heterologous DNA into a suitable host cell. Once in the host cell, the vector can replicate independently of or coincidental with the host chromosomal DNA, and several copies of the vector and its inserted DNA can be generated. In addition, the vector can also contain the necessary elements that permit transcription of the inserted DNA into an mRNA molecule or otherwise cause replication of the inserted DNA into multiple copies of RNA. Some expression vectors additionally contain sequence elements adjacent to the inserted DNA that increase the half-life of the expressed mRNA and/or allow translation of the mRNA into a protein molecule. Many molecules of mRNA and polypeptide encoded by the inserted DNA can thus be rapidly synthesized.

The terms "nucleic acid" or "polynucleotide" can be used interchangeably and refer to a polymer that can be corresponded to a ribose nucleic acid (RNA) or deoxyribose nucleic acid (DNA) polymer, or an analog thereof. This includes polymers of nucleotides such as RNA and DNA, as well as synthetic forms, modified (e.g., chemically or biochemically modified) forms thereof, and mixed polymers (e.g., including both RNA and DNA subunits). Exemplary modifications include methylation, substitution of one or more of the naturally occurring nucleotides with an analog, internucleotide modifications such as uncharged linkages (e.g., methyl phosphonates, phosphotriesters, phosphoamidates, carbamates, and the like), pendent moieties (e.g., polypeptides), intercalators (e.g., acridine, psoralen, and the like), chelators, alkylators, and modified linkages (e.g., alpha anomeric nucleic acids and the like). Also included are synthetic molecules that mimic polynucleotides in their ability to bind to a designated sequence via hydrogen bonding and other chemical interactions. Typically, the nucleotide monomers are linked via phosphodiester bonds, although synthetic forms of nucleic acids can comprise other linkages (e.g., peptide nucleic acids as described in Nielsen et al. (Science 254:1497-1500, 1991). A nucleic acid can be or can include, e.g., a chromosome or chromosomal segment, a vector (e.g., an expression vector), an expression cassette, a naked DNA or RNA polymer, the product of a polymerase chain reaction (PCR), an oligonucleotide, a probe, and a primer. A nucleic acid can be, e.g., single-stranded, double-stranded, or triple-stranded and is not limited to any particular length. Unless otherwise indicated, a particular nucleic acid sequence comprises or encodes complementary sequences, in addition to any sequence explicitly indicated.

The term "glycosylation" denotes the chemical reaction of covalently coupling a glycosyl residue to an acceptor group. One specific acceptor group is a hydroxyl group, e.g. a hydroxyl group of another sugar. "Sialylation" is a specific form of glycosylation wherein the acceptor group is reacted with a sialic acid (=N-acetylneuraminic acid) residue. Such a reaction is typically catalyzed by a sialyltransferase enzyme using cytidine-5'-monophospho-N-acetylneuraminic acid as donor compound or co-substrate.

"Sialylation" is a specific embodiment of a result of glycosyltransferase enzymatic activity (sialyltransferase enzymatic activity in the particular case), under conditions permitting the same. Generally, the skilled person appreciates that the aqueous buffer in which a glycosyltransferase enzymatic reaction can be performed (="permitting glycosyltransferase enzymatic activity") needs to be buffered using a buffer salt such as Tris, MES, phosphate, acetate, or another buffer salt specifically capable of buffering in the pH range of pH 6 to pH 8, more specifically in the range of pH 6 to pH 7, even more specifically capable of buffering a solution of about pH 6.5. The buffer may furher contain a neutral salt such as but not limited to NaCl. Further, in particular embodiments the skilled person may consider adding to the aqueous buffer a salt comprising a divalent ion such as $Mg^{2+}$ or $Mn^{2+}$, e.g. but not limited to $MgCl_2$ and $MnCl_2$. Conditions permitting glycosyltransferase enzymatic activity known to the art include ambient (room) temperature, but more generally temperatures in the range of 0° C. to 40° C., particularly 10° C. to 30° C., particularly 20° C.

The term "glycan" refers to a poly- or oligosaccharide, i.e. to a multimeric compound which upon acid hydrolysis yields a plurality of monosachharides. A glycoprotein comprises one or more glycan moieties which are covalently coupled to side groups of the polypeptide chain, typically via asparagine or arginine ("N-linked glycosylation") or via serine or threonine ("O-linked glycosylation").

The use of glycosyltransferases for enzymatic synthesis of complex glycan structures is an attractive approach to obtain complex bioactive glycoproteins. E.g. Barb et al. Biochemistry 48 (2009) 9705-9707 prepared highly potent sialylated forms of the Fc fragment of immunoglobulin G using isolated human ST6Gal-I. However, growing interest in the therapeutic application of glycosyltransferases leads to an increasing demand of glycosyltransferases including sialyltransferases. Different strategies to increase or modify the sialylation of glycoproteins were described by Bork K. et al. J. Pharm. Sci. 98 (2009) 3499-3508. An attractive strategy is sialylation in vitro of recombinantly produced proteins (such as but not limited to immunoglobulins and growth factors), particularly therapeutic proteins. To this end, several research groups described expression of sialyltransferases in transformed organisms and purification of the recombinantly produced sialyltransferases. As glycosyltransferases of prokaryotic origin usually do not act on complex glycoproteins (e.g. antibodies), sialyltransferases from mammalian origin were studied with preference.

Particular glycoproteins subject to the disclosures and all aspects of the present document and the aspects and embodiments herein comprise without limitation cell surface glycoproteins and glycoproteins present in soluble form in serum ("serum glycoprotein"), the glycoproteins particularly being of mammalian origin. A "cell surface glycoprotein" is understood to be glycoprotein of which a portion is located on and bound to the surface of a membrane, by way of a membrane anchor portion of the surface glycoprotein's polypeptide chain, wherein the membrane is part of a biological cell. The term cell surface glycoprotein also encompasses isolated forms of the cell surface glycoprotein as well as soluble fragments thereof which are separated from the membrane anchor portion, e.g. by proteolytic cleavage or by recombinant production of such soluble fragments. A "serum glycoprotein" is understood as a glycoprotein being present in serum, i.e. a blood protein present in the non-cellular portion of whole blood, e.g. in the supernatant following sedimentation of cellular blood components. Without limitation, a specifically regarded and embodied serum glycoprotein is an immunoglobulin. Particular immunoglobulins mentioned in here belong to the IgG group (characterized by Gamma heavy chains), specifically any of four the IgG subgroups. For the disclosures, aspects and embodiments herein the term "serum glycoprotein also encompasses a monoclonal antibody; monoclonal antibodies artificially are well known to the art and can be produced e.g. by hybridoma cells or recombinantly using transformed host cells. A further serum specific glycoprotein is a carrier protein such as serum albumin, a fetuin, or another glycoprotein member of the superfamily of histidine-rich glycoproteins of which the fetuins are members. Further, without limitation, a specifically regarded and embodied serum glycoprotein regarding all disclosures, aspects and embodiments herein is a glycosylated protein signaling molecule. A particular molecule of this group is erythropoietin (EPO).

For in vitro engineering of glycoproteins glycosyltransferases can be used as an efficient tool (Weijers 2008). Glycosyltransferases of mammalian origin are compatible with glycoproteins as substrates whereas bacterial glycosyltransferases usually modify simpler substrates like oligosaccharides. For this reason synthetic changes in the glycan moieties of glycoproteins are advantageously made using mammalian glycosyltransferases as tools of choice. However, for a large scale application of glycosyltransferases in glycoengineering availability of suitable enzymes in large (i.e. industrial) quantities is required. The disclosure herein particularly provides a protein with (i) hST6Gal-I sialyltransferase activity and (ii) sialidase activity which can be used for quantitatively controlled in vitro sialylation of target glycoproteins with one or more accessible galactosyl substrate moiety/moieties. Suitable targets include on the one hand asialoglycoproteins, i.e. glycoproteins from which sialic acid residues have been removed by the action of sialidases. On the other hand, bi-sialylated glycoproteins may serve as substrate for sialidase activity. Very advantageously, asialo-, mono-sialylated and bi-sialylated immunoglobulins are specific substrates, particularly immunoglobulins of the IgG class.

While expressing wild-type hST6Gal-I in the methylotrophic yeast *Pichia pastoris* and having targeted the expressed polypeptide to the secretory pathway of the host organism, different truncated variants of recombinantly produced hST6Gal-I were observed. Generally, hST6Gal-I derived proteins were chromatographically purified and analyzed, particularly by means of mass spectrometry and by way of determining the amino acid sequence from the N-terminus (Edman degradation). By these means truncations, particularly N-terminal truncations of hST6Gal-I were characterized in detail.

Several remarkable truncation variants were identified in the supernatants of transformed *Pichia* strains. The variants could possibly result from site-specific proteolytic cleavage during the course of secretion from the yeast cells, or result from endoproteolytic cleavage by one or more extracellular protease(s) present in the supernatant of cultured *Pichia* strains.

Each identified truncation variant was given a "delta" (="Δ") designation indicating the number of the last amino acid position of the respective truncation deletion, counted from the N-Terminus of the wild-type hST6Gal-I polypeptide according to SEQ ID NO:1 The particular N-terminal truncation variant Δ89 of hST6Gal-I was studied in more detail.

Expression vectors were constructed for expression of hST6Gal-I wild-type protein as well as of the Δ89 truncation variant in various host organisms including prokaryotes such as *E. coli* and *Bacillus* sp., yeasts such as *Saccharomyces cerevisiae* and *Pichia* pastoris, and mammalian cells such as CHO cells and HEK cells. Vectors with expression constructs for the Δ89 truncation variant of hST6Gal-I were assembled molecularly thereby providing the means of recombinantly producing the Δ89 variant of human ST6Gal-I in several expression systems. To facilitate purification of the recombinantly expressed enzyme, i.e. the truncation variant polypeptide encoded by the constructs optionally included a N-terminal His-tag.

In a particular series of experiments, expression constructs were inserted into vectors for propagation in *Pichia pastoris* strain KM71H. Expression typically was controlled by an inducible promoter such as the AOX1 promoter. His-tagged truncation variants were additionally fused to a leader peptide capable of targeting the expressed primary translation product to the secretory pathway of the transformed host. Posttranslational processing thus included secretion of the His-tagged truncation variant into the surrounding medium while the leader peptide was cleaved off by an endoprotease of the secretion machinery.

Transformed *Pichia* cells were typically cultured in a liquid medium. After induction of expression, the transformed cells were cultured for a certain time to produce the respective target protein. Following the termination of the culturing step, the cells and other insoluble materials present in the culture were separated from the supernatant. The truncation variant Δ89 hST6Gal-I in the cleared supernatants was analyzed. However, attempts to purify the enzyme from the supernatant failed when a chromatography column loaded with a Ni-chelating affinity matrix was used, as the active enzyme was not retained on the column but was found in the flow-through. Purification of the enzymes (wild type and variants) using a cation exchange resin nevertheless resulted in highly enriched enzyme preparations. But this purification procedure generally appeared to affect the activity of the enzyme negatively.

An aspect and a specific embodiment of all other aspects as disclosed herein is a variant mammalian glycosyltransferase capable of catalyzing hydrolysis of the α2,6 glycosidic bond of a N-acetylneuraminyl-α2,6-β-D-galactosyl-1,4-N-acetyl-β-D-glucosamine moiety of a glycan in a glycoprotein. Particularly, the variant mammalian glycosyltransferase is capable of catalyzing formation? of the α2,6 glycosidic bond of a N-acetylneuraminyl-α2,6-β-D-galactosyl-1,4-N-acetyl-β-D-glucosamine moiety in a glycoprotein glycan, thereby generating free? N-acetylneuraminic acid. In a specific embodiment of all aspects as disclosed herein, the variant mammalian glycosyltransferase capable of catalyzing hydrolysis of the α2,6 glycosidic bond is a mammalian glycosyltransferase is derived, by way of amino acid deletion, from human β-galactoside-α-2,6-sialyltransferase I according to SEQ ID NO:1, said sequence being truncated by a deletion from the N-terminus. In a further specific embodiment of all aspects as disclosed herein, the truncation deletion from the N-terminus is the contiguous sequence of position 1 to position 89 of SEQ ID NO:1.

Another aspect and a specific embodiment of all other aspects as disclosed herein is a fusion polypeptide comprising a polypeptide of a variant mammalian glycosyltransferase according to any embodiment as disclosed herein. A fusion protein or fusion polypeptide is a chimeric polypeptide comprising amino acid sequences of two or more polypeptides. The two or more polypeptides may have complementary functions, one of the polypeptides may provide a supplementary functional property, or one of the polypeptides may have a function unrelated to the others in the fusion polypeptide. One or more polypeptides comprising organelle targeting or retention sequences may be fused with a desired polypeptide to target the desired polypeptide to a specific cellular organelle, or retain the desired polypeptide within the cell. One or more polypeptides comprising a carrier sequence that aids in expression, purification and/or detection of the fusion polypeptide may be fused with a desired polypeptide (e.g., FLAG, a myc tag, a 6×His tag, GST fusions and the like). Particular fusion partners include N-terminal leader peptides capable of directing the variant mammalian glycosyltransferase portion of the fusion polypeptide to the secretory pathway of the host organism in which the fusion polypeptide is expressed. Thereby secretion in the extracellular space and the surrounding medium is facilitated. Yet, another aspect and a specific embodiment of all other aspects as disclosed herein is a nucleotide sequence encoding a variant mammalian glycosyltransferase according to any embodiment as disclosed herein or a fusion polypeptide comprising as a portion a variant mammalian glycosyltransferase according to any embodiment as disclosed herein. In a specific embodiment of all aspects as disclosed herein the nucleotide sequence includes the sequence of position 95 to position 1048 of SEQ ID NO:3.

Yet, another aspect and a specific embodiment of all other aspects as disclosed herein is an expression vector comprising a target gene and sequences facilitating expression of the target gene in a host organism transformed with the expression vector, wherein the target gene comprises a nucleotide sequence as disclosed herein.

Yet, another aspect and a specific embodiment of all other aspects as disclosed herein is a transformed host organism, wherein the host organism is transformed with an expression vector as disclosed herein. With particular advantage, Human Embryonic Kidney 293 (HEK) cells can be used to practice the teachings as disclosed in here. A particular advantage of these cells is that they are very suited targets for transfection followed by subsequent culture and transient expression of the target gene. Thus, HEK cells can be efficiently used to produce target proteins by way of recombinant expression. With great advantage, expression constructs are designed to direct the translation products to the secretory pathway leading to secretion of the variant mammalian glycosyltransferase or a fusion polypeptide as disclosed herein. Nevertheless, Jurkat, NIH3T3, HeLa, COS and Chinese Hamster Ovary (CHO) cells are well-known alternatives and are included herein as alternative host organisms for transformation and specific embodiments of all aspects as disclosed herein.

Yet, another aspect and a specific embodiment of all other aspects as disclosed herein is a method to produce recombinantly a variant mammalian glycosyltransferase, the method comprising the step of expressing in a host organism transformed with an expression vector a nucleotide sequence encoding a variant mammalian glycosyltransferase as disclosed herein, wherein a polypeptide is formed, thereby producing variant mammalian glycosyltransferase.

According to earlier knowledge, N-terminally truncated variants of glycosyltransferases are advantageously used in vitro due to their lack of transmembrane domains. Thus, such variants are useful for catalyzing and performing glycosyltransferase reactions in solution. It was surprisingly found and is disclosed herein that specifically the N-terminally truncated variant Δ89 hST6Gal-I displays different activities in vitro, e.g. when incubated with glycosylated antibodies. Thus, a specific embodiment of the present disclosure and all aspects and embodiments herein is a variant mammalian glycosyltransferase capable of catalyzing hydrolysis of a α2,6 glycosidic bond of a N-acetylneuraminyl-α2,6-β-D-galactosyl-1,4-N-acetyl-β-D-glucosamine moiety of a bi-sialylated glycoprotein, i.e. a glycoprotein comprising two separate terminal N-acetylneuraminyl-α2,6-β-D-galactosyl-1,4-N-acetyl-β-D-glucosamine moieties in one or more glycan portion(s) of the glycoprotein. In a specific embodiment, only one α2,6 glycosidic bond in a is hydrolyzed. In a further specific embodiment, the bi-sialylated glycoprotein is a bi-sialylated IgG immunoglobulin.

As an exemplary case, the IgG-Fc glycan G2 has two galactose moieties at the termini of the antennate branches which can be sialylated. Under suitable reaction conditions, the N-terminally truncated variant Δ89 hST6Gal-I catalyzes the synthesis of IgG with bi-sialylated G2 glycans (G2+2SA) at the immunoglobulin Fc portion. However, when extending the incubation time the enzyme variant acts as a sialidase capable of removing one sialic acid moiety from the bi-sialylated (G2+2SA) antibodies resulting in mono-sialylated (G2+1SA) antibodies. This activity was found unexpectedly and appears to represent an intrinsic sialidase (neuraminidase) activity, which so far has not been described for mammalian ST6Gal-I enzymes.

In a basic publication on human ST6Gal-I it was stated that the enzyme does not contain any sialidase activity, see Sticher et al. Glycoconjugate Journal 8 (1991) 45-54. In view of the present surprising finding it becomes possible to preferentially synthesize glycoproteins with mono- or bi-sialylated glycans, using the same enzyme and controlling the reaction kinetics of the enzyme. A further advantage is that both activities, sialylation activity and sialidase activity are provided by the same enzyme, in the same reaction vessel.

Figure 2:
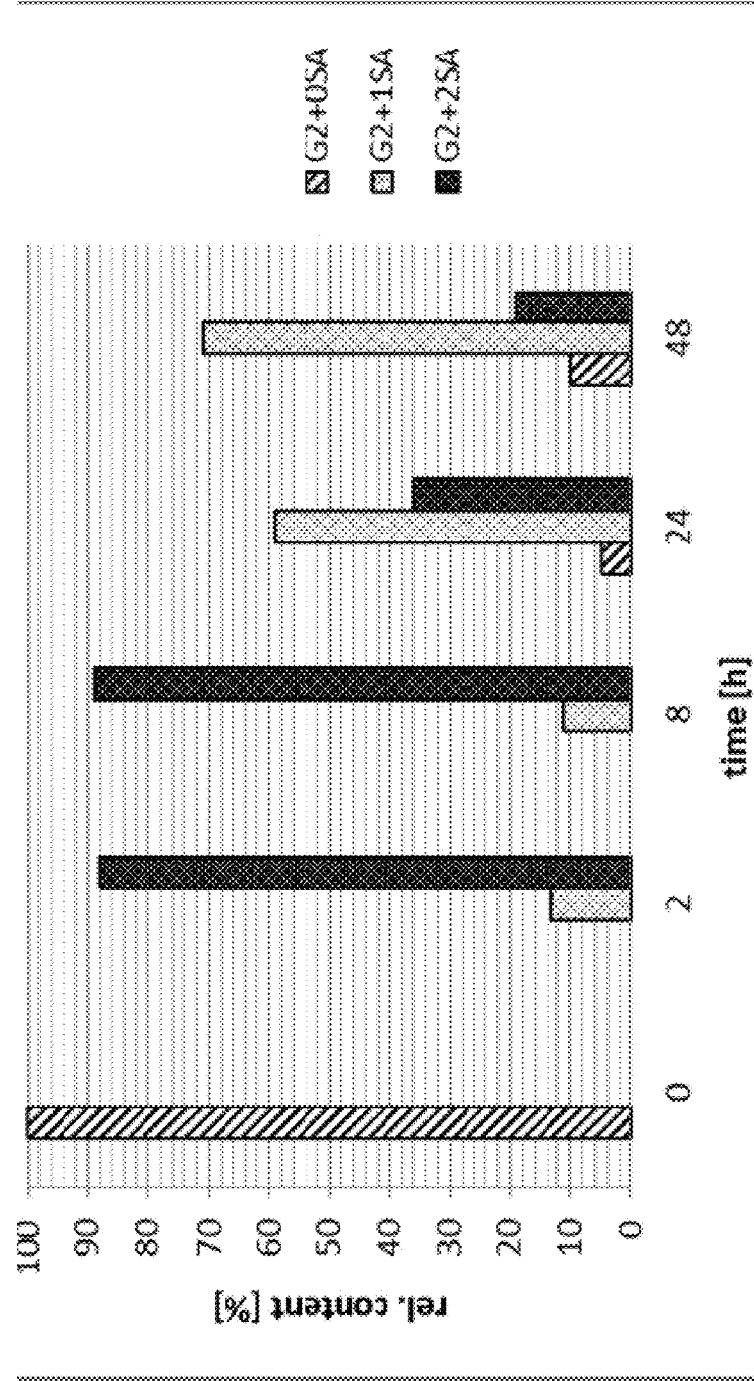
FIG. 2 Time course of sialylation of MAB <IL-1R> using recombinant Δ89 hST6Gal-I.

The general finding documented in the present disclosure is, however, that there exists a variant mammalian glycosyltransferase, specifically a glycosyltransferase according to the present disclosure, which is capable of catalyzing hydrolysis of the α2,6 glycosidic bond of a N-acetylneuraminyl-α2,6-β-D-galactosyl-1,4-N-acetyl-β-D-glucosamine moiety of a glycan in a glycoprotein. In addition to the already known sialyltransferase (sialylation) activity the surprising finding was that at least as specifically shown for the N-terminally truncated human β-galactoside-α-2,6-sialyltransferase I having the amino acid sequence of SEQ ID NO:2 there is not only conventional sialyltransferase but also sialidase enzymatic activity mediated by this enzyme. Interestingly, in the exemplary cases these two activities were not observed at the same time, which may partly explain the unexpected finding. As shown in FIG. 2, sialyltransferase activity dominates in the beginning and sialidase activity becomes apparent only at a later stage during the incubation, the reason for which is not clear at this point. Nevertheless, the apparent recognition of two distinct activities of the same enzyme allows to control the extent of sialylation of target molecules, e.g. by way of varying incubation time.

Thus, another aspect and a specific embodiment of all other aspects as disclosed herein is the use of a variant mammalian glycosyltransferase as disclosed herein, specifically the N-terminally truncated human β-galactoside-α-2,6-sialyltransferase I having the amino acid sequence of SEQ ID NO:2, for hydrolyzing the α2,6 glycosidic bond in a N-acetylneuraminyl-α2,6-β-D-galactosyl-1,4-N-acetyl-β-D-glucosamine moiety, the moiety being a terminal structure of a glycan in a sialylated glycoprotein or glycolipid. In a specific embodiment, the sialylated glycoprotein or glycolipid is a bi-sialylated glycoprotein or glycolipid, respectively.

A specific embodiment of such use and furthermore another specific embodiment of all aspects as disclosed herein is a method for hydrolyzing the α2,6 glycosidic bond in a N-acetylneuraminyl-α2,6-β-D-galactosyl-1,4-N-acetyl-β-D-glucosamine moiety, the moiety being a terminal structure of a glycan in a sialylated glycoprotein or glycolipid, the method comprising the steps of (a) providing in an aqueous solution a sialylated glycoprotein or glycolipid with a terminal N-acetylneuraminyl-α2,6-β-D-galactosyl-1,4-N-acetyl-β-D-glucosamine moiety in the glycan portion of said glycoprotein; and (b) incubating the N-acetylneuraminyl-α2,6-β-D-galactosyl-1,4-N-acetyl-β-D-glucosamine moiety with a variant mammalian glycosyltransferase as disclosed herein; thereby hydrolyzing the α2,6 glycosidic bond in the N-acetylneuraminyl-α2,6-β-D-galactosyl-1,4-N-acetyl-β-D-glucosamine moiety. Specifically, the sialyl residue to be released by the hydrolysis reaction is connected with an α2,6 bond to the β-D-galactosyl-1,4-N-acetyl-β-D-glucosamine at the terminus of the antennal structure in the glycan.

In a specific embodiment and with particular advantage, the variant mammalian glycosyltransferase is the N-terminally truncated human β-galactoside-α-2,6-sialyltransferase I having the amino acid sequence of SEQ ID NO:2. In a further specific embodiment, catalysis of the hydrolysis reaction and the glycosyltransferase activity take place in a competitive fashion. Considering substrate target molecules with two or more acceptor sites for sialylation it is however remarkable that by way of glycosyltransferase activity all possible sites become sialylated, as long as there is sufficient donor compound available to promote the reaction. This property of the N-terminally truncated human β-galactoside-α-2,6-sialyltransferase I having the amino acid sequence of SEQ ID NO:2 is exemplified by the disclosure herein. Thus, bi-sialylated IgG molecules are predominanrtly obtained in an exemplary incubation of a sialylation reaction which lasted 8 hours. After an incubation time of more than 8 hours or longer, however, a growing quantity of mono-sialylated IgG molecules was observed. One possible conclusion could be that the ratio of mono- and bi-sialylated IgG molecules is the result of a dynamic equilibrium of two competing reactions: transfer and hydrolysis. Alternatively, the conditions in the sialylation reaction mixture may change with time, e.g. as a possible result of donor compound exhaustion. Nevertheless, it is remarkable that a substantial amount of mono-sialylated IgG molecules is retained, even after prolonged incubation of 72 hours, as exemplified.

In a specific embodiment of all aspects as disclosed herein, there is provided a method of producing in vitro a sialylated target molecule with a controlled quantity of sialyl residues, the method comprising the steps of (a) providing a glycosylated target molecule in an aqueous solution and under conditions permitting glycosyltransferase enzymatic activity, the target molecule being selected from a glycoprotein and a glycolipid, the target molecule comprising a plurality of antennae, at least two of the antennae each having as terminal structure a β-D-galactosyl-1,4-N-acetyl-β-D-glucosamine moiety with a hydroxyl group at the C6 position in the galactosyl residue; (b) forming one or more terminal antennal N-acetylneuraminyl-α2,6-β-D-galactosyl-1,4-N-acetyl-β-D-glucosamine residues by incubating the target molecule of step (a) for a first pre-determined time with N-terminally truncated human β-galactoside-α-2,6-sialyltransferase I having the amino acid sequence of SEQ ID NO:2 and in the presence of cytidine-5'-monophospho-N-acetylneuraminic acid, or a functional equivalent thereof, as donor compound thereby providing a sialylated target molecule; hydrolyzing the α2,6 glycosidic bond in one or more terminal antennal N-acetylneuraminyl-α2,6-β-D-galactosyl-1,4-N-acetyl-β-D-glucosamine residues by incubating the sialylated target molecule of step (b) for a second pre-determined time with the N-terminally truncated human β-galactoside-α-2,6-sialyltransferase I having the amino acid sequence of SEQ ID NO:2; thereby producing in vitro the sialylated target molecule with a controlled quantity of sialyl residues.

Such controlled sialylation is provided as a novel means to synthesize in vitro mono-, bi-, and higher sialylated glycoproteins with a desired degree of sialylation. Thus, though exemplified by showing the desired technical effects with IgG molecules, the uses according to the disclosures in here also allow to process other glycoproteins in a similar way, with the proviso that concerning glysosyltransferase activity, the glycoproteins comprise two or more terminal antennate β-D-galactosyl-1,4-N-acetyl-β-D-glucosamine moieties. The same reasoning applies in an analogous way to glycolipids.

In a particular example, recombinant humanized IgG1 and IgG4 monoclonal antibodies (mabs), characterized as G2+0SA (=no sialylation at acceptor site), as well as EPO (=erythropoietin) were used as targets in sialylation experiments (30 μg enzyme/300 μg target protein). Δ89 hST6Gal-I was used under standard reaction conditions and the G2+0SA, G2+1SA (mono-sialylation) and G2+2SA (bi-sialylation) status was analyzed by mass spectrometry.

Due to the high expression rates and the efficient purification procedures Δ89 hST6Gal-I is available in large quantities and with high purity. The variant enzyme is active with high molecular weight substrates of which monoclonal antibodies are just one example. Depending on the incubation time, Δ89 hST6Gal-I shows different performance in sialylation experiments using monoclonal antibodies with bi-antennary glycan as substrate. Using the variant Δ89 preferably bi-sialylated glycans are obtained with great advantage after shorter incubation periods, whereas under identical conditions using Δ89 mono-sialylated glycans are obtained after longer incubation periods.

Tetra-antennary glycans are also accepted as substrate (data not shown). The results demonstrate that both variants can be successfully used for in vitro glycoengineering of therapeutic antibodies.

By practicing teachings as provided herein, recombinant Δ89 variant of human ST6-Gal-I is an enzyme available in large quantities. Together with the already available donor substrates (activated sugars used as co-substrates), a highly advantageous set of reagents is provided for quantitatively controlled in vitro glycoengineering of proteins.

The following items further provide specific aspects of the disclosure, and specific embodiments to practice the teachings provided herein.

1. A variant mammalian glycosyltransferase capable of catalyzing hydrolysis of the α2,6 glycosidic bond of a N-acetylneuraminyl-α2,6-β-D-galactosyl-1,4-N-acetyl-β-D-glucosamine moiety of a glycan in a glycoprotein.
2. The variant mammalian glycosyltransferase according to item 1, further being capable of catalyzing formation of the α2,6 glycosidic bond of a N-acetylneuraminyl-α2,6-β-D-galactosyl-1,4-N-acetyl-β-D-glucosamine moiety in a glycoprotein glycan.
3. The variant mammalian glycosyltransferase according to any of the items 1 and 2, wherein the hydrolysis generates free N-acetylneuraminic acid.
4. The variant mammalian glycosyltransferase according to any of the items 1 to 3, wherein the formation of the α2,6 glycosidic bond is effected by reacting the N-acetylneuraminic acid residue of the donor compound cytidine-5'-monophospho-N-acetylneuraminic acid with the hydroxyl group at the C6 position in a terminal galactosyl residue of the acceptor group β-D-galactosyl-1,4-N-acetyl-β-D-glucosamine, the acceptor group being a moiety of the glycoprotein glycan.
5. The variant mammalian glycosyltransferase according to any of the items 1 to 3, wherein the variant mammalian glycosyltransferase is derived, by way of amino acid exchange or amino acid deletion, from human β-galactoside-α-2,6-sialyltransferase I having the amino acid sequence according to SEQ ID NO:1.
6. The variant mammalian glycosyltransferase according to item 5, wherein the polypeptide of the variant comprises an amino acid sequence of the wild-type mammalian glycosyltransferase having the amino acid sequence according to SEQ ID NO:1 truncated by a deletion from the N-terminus.
7. The variant mammalian glycosyltransferase according to item 6, wherein the deletion from the N-terminus is the sequence of position 1 to position 89 of SEQ ID NO:1.
8. The variant mammalian glycosyltransferase according to any of the items 6 and 7, wherein the polypeptide of the variant is the amino acid sequence of SEQ ID NO: 2.
9. The variant mammalian glycosyltransferase according to any of the items 1 to 8, wherein the N-terminus or C-terminus of the polypeptide of the variant is fused to an affinity tag.

10. The variant mammalian glycosyltransferase according to item 9, wherein the affinity tag comprises four, five, six or more consecutive histidine residues.
11. The variant mammalian glycosyltransferase according to any of the items 9 and 10, wherein a peptidase cleavage site is located between the affinity tag and the N-terminus or C-terminus of the polypeptide of the variant.
12. The variant mammalian glycosyltransferase according to any of the items 1 to 11, wherein the polypeptide of the variant further comprises a N-terminal methionine residue.
13. A fusion polypeptide comprising the polypeptide of a variant mammalian glycosyltransferase according to any of the items 1 to 12.
14. A nucleotide sequence encoding the polypeptide of a variant mammalian glycosyltransferase according to any of the items 1 to 12.
15. A nucleotide sequence encoding the polypeptide of a fusion polypeptide comprising the polypeptide of a variant mammalian glycosyltransferase according to any of the items 1 to 12.
16. An expression vector comprising a target gene operably linked to sequences facilitating expression of the target gene in a host organism transformed with the expression vector, wherein the target gene comprises a nucleotide sequence according to any of the items 14 and 15.
17. A transformed host organism, wherein the host organism is transformed with an expression vector according to item 16.
18. The transformed host organism according to item 17, wherein the organism is selected from a yeast cell and a mammalian cell.
19. The transformed host organism according to item 19, wherein the organism is a mammalian cell selected from the group consisting of a HEK cell, a Jurkat cell, a NIH3T3 cell, COS cell, a CHO cell, and a HeLa cell.
20. A method to recombinantly produce a variant mammalian glycosyltransferase capable of catalyzing hydrolysis of the α2,6 glycosidic bond of a N-acetylneuraminyl-α2,6-β-D-galactosyl-1,4-N-acetyl-β-D-glucosamine moiety of a glycan in a glycoprotein, the method comprising the step of expressing in a transformed host organism a nucleotide sequence encoding the variant mammalian glycosyltransferase according to any of the items 1 to 12, wherein a polypeptide is formed, thereby producing the variant mammalian glycosyltransferase.
21. The method according to item 20, wherein the produced enzyme is secreted from the host organism.
22. The method according to any of the items 20 and 21, wherein the host organism is a eukaryotic cell.
23. The method according to item 22, wherein the host organism is selected from a yeast cell and a mammalian cell.
24. The method according to item 23, wherein the host organism is a mammalian cell selected from the group consisting of a HEK cell, a COS cell, a CHO cell, and a HeLa cell.
25. The method according to any of the items 20 to 24, wherein the variant mammalian glycosyltransferase is purified.
26. Use of a variant mammalian glycosyltransferase according to any of the items 1 to 12, or a fusion protein according to item 13, for hydrolyzing the α2,6 glycosidic bond in a N-acetylneuraminyl-α2,6-β-D-galactosyl-1,4-N-acetyl-β-D-glucosamine moiety, the moiety being a terminal structure of a glycan in a sialylated glycoprotein or glycolipid.
27. The use according to item 26, wherein the variant mammalian glycosyltransferase is the N-terminally truncated human β-galactoside-α-2,6-sialyltransferase I having the amino acid sequence of SEQ ID NO:2.
28. The use according to any of the items 26 and 27, wherein the glycoprotein is selected from the group consisting of a cell surface glycoprotein, a glycosylated protein signaling molecule, a glycosylated immunoglobulin, and a glycosylated protein of viral origin.
29. The use according to any of the items 26 and 27, wherein the glycoprotein is selected from the group consisting of IgG1, IgG2, IgG3, IgG4, EPO, and Asialofetuin.
30. A method to hydrolyze the α2,6 glycosidic bond in a N-acetylneuraminyl-α2,6-β-D-galactosyl-1,4-N-acetyl-β-D-glucosamine moiety, the moiety being a terminal structure of a glycan in a sialylated glycoprotein or glycolipid, the method comprising the steps of
(a) providing in an aqueous solution a sialylated, and in a particular embodiment a bi-sialylated glycoprotein or glycolipid with a terminal N-acetylneuraminyl-α2,6-β-D-galactosyl-1,4-N-acetyl-β-D-glucosamine moiety in the glycan portion of said glycoprotein;
(b) incubating the N-acetylneuraminyl-α2,6-β-D-galactosyl-1,4-N-acetyl-β-D-glucosamine moiety with a variant mammalian glycosyltransferase according to any of the items 1 to 12;
thereby hydrolyzing the α2,6 glycosidic bond in the N-acetylneuraminyl-α2,6-β-D-galactosyl-1,4-N-acetyl-β-D-glucosamine moiety.
31. The method according to item 30, wherein the variant mammalian glycosyltransferase is the N-terminally truncated human β-galactoside-α-2,6-sialyltransferase I having the amino acid sequence of SEQ ID NO:2.
32. The method according to any of the items 30 and 31, wherein the glycoprotein is selected from the group consisting of a cell surface glycoprotein, a glycosylated protein signaling molecule, a glycosylated immunoglobulin, and a glycosylated protein of viral origin.
33. The method according to any of the items 30 to 32, wherein step (a) is performed under conditions permitting glycosyltransferase enzymatic activity.
34. The method according to any of the items 30 to 33, wherein step (b) is performed under conditions permitting glycosyltransferase enzymatic activity.
35. A method of producing in vitro a sialylated target molecule with a controlled quantity of sialyl residues, the method comprising the steps of
(a) providing a glycosylated target molecule in an aqueous solution and under conditions permitting glycosyltransferase enzymatic activity, the target molecule being selected from a glycoprotein and a glycolipid, the target molecule comprising a plurality of antennae, at least two of the antennae each having as terminal structure a β-D-galactosyl-1,4-N-acetyl-β-D-glucosamine moiety with a hydroxyl group at the C6 position in the galactosyl residue;
(b) forming one or more terminal antennal N-acetylneuraminyl-α2,6-β-D-galactosyl-1,4-N-acetyl-β-D-glucosamine residues by incubating the target molecule of step (a) for a first pre-determined time with N-terminally truncated human β-galactoside-α-2,6-sialyltransferase I having the amino acid sequence of SEQ ID NO:2 and in the presence of cytidine-5'- monophospho-N-acetylneuraminic acid, or a functional equivalent thereof, as donor compound thereby providing a sialylated target molecule;
(c) hydrolyzing the α-2,6 glycosidic bond in one or more terminal antennal N-acetylneuraminyl-α2,6-β-D-galactosyl-1,4-N-acetyl-β-D-glucosamine residues by incubating the sialylated target molecule of step (b) for a second pre-determined time with the N-terminally truncated human β-galactoside-α-2,6-sialyltransferase I having the amino acid sequence of SEQ ID NO:2;
thereby producing in vitro the sialylated target molecule with a controlled quantity of sialyl residues.

36. The method according to item 35, wherein between the steps (b) and (c) sialylation of the target molecule is determined quantitatively.

37. The method according to any of the items 35 and 36, wherein after step (c) sialylation of the target molecule is determined quantitatively.

38. The method according to any of the items 35 to 37, wherein steps (a), (b) and (c) are performed continuously in the same vessel.

39. The method according to any of the items 35 to 38, wherein the target molecule is a purified immunoglobulin molecule.

40. The method according to item 39, wherein a single immunoglobulin molecule comprises two antennae, each antenna having as terminal structure a β-D-galactosyl-1,4-N-acetyl-β-D-glucosamine moiety with a hydroxyl group at the C6 position in the galactosyl residue.

41. The method according to item 40, wherein the immunoglobulin molecule is of the IgG class.

42. The method according to item 41, wherein steps (a), (b) and (c) are performed continuously in the same vessel with a measured amount of target molecules, wherein step (b) is performed for 0 h to about 24 h and subsequent step (c) is performed for 0 h, and wherein the relative amount of bi-sialylated target molecules is about 35% to about 90%.

43. The method according to item 42, wherein step (b) is performed for about 0 h to 2 h, and wherein the relative amount of bi-sialylated target molecules is about 80% to about 90%.

44. The method according to item 42, wherein step (b) is performed for about 2 h to 8 h, and wherein the relative amount of bi-sialylated target molecules is about 80% to about 90%.

45. The method according to any of the items 42 to 44, wherein the relative amount of mono-sialylated target molecules is about 10% to about 60%.

46. The method according to any of the items 43 and 44, wherein the relative amount of mono-sialylated target molecules is about 10% to about 15%.

47. The method according to item 41, wherein steps (a), (b) and (c) are performed continuously in the same vessel with a measured amount of target molecules, wherein step (b) is performed for 24 h and subsequent step (c) is performed for 0 h to about 72 h or longer, and wherein the relative amount of mono-sialylated target molecules is about 60% to about 75%.

48. The method according to item 47, wherein step (c) is performed for about 0 h to 24 h, and wherein the relative amount of mono-sialylated target molecules is about 60% to about 70%.

49. The method according to item 47, wherein step (c) is performed for about 24 h to 48 h, and wherein the relative amount of mono-sialylated target molecules is about 70% to about 75%.

50. The method according to any of the items 47 to 49, wherein the relative amount of bi-sialylated target molecules is about 20% to about 35%.

51. The method according to any of the items 48 and 49, wherein the relative amount of bi-sialylated target molecules is about 10% to about 20%.

52. The method according to any of the items 42 to 49, wherein the weight-by-weight [w/w] ratio of target (immunoglobulin) molecules : human β-galactoside-α-2,6-sialyltransferase I molecules is 10:1, wherein each has a relative purity of 80% or higher.

53. A preparation of glycosylated target molecules, the target molecules being immunoglobulin molecules of the IgG class, wherein the amount of bi-sialylated target molecules is about 35% to about 90%, the preparation being obtained by a method according to any of the items 41-46.

54. A preparation of glycosylated target molecules, the target molecules being immunoglobulin molecules of the IgG class, wherein the amount of mono-sialylated target molecules is about 60% to about 75%, the preparation being obtained by a method according to any of the items 47-51.

55. A preparation of sialylated target molecules, the target molecules being immunoglobulin molecules of the IgG class, wherein the amounts of mono-and bi-sialylated target molecules are controlled quantities, the preparation being obtained by a method according to any of the items 41-51.

56. Use of a preparation of sialylated immunoglobulin molecules according to item 55 for preparing a pharmaceutical composition.

57. A method of producing in vitro a sialylated target molecule with a controlled quantity of sialyl residues, comprising the steps of performing a method according to any of the items 35 to 52, wherein step (c) is followed by a step (d) comprising adding to the aqueous solution a measured amount of cytidine triphosphate (CTP), thereby inhibiting the N-terminally truncated human β-galactoside-α-2,6-sialyltransferase I having the amino acid sequence of SEQ ID NO:2, thereby producing in vitro the sialylated target molecule with a controlled quantity of sialyl residues.

58. The method according to item 57, wherein the concentration of CTP in the aqueous solution is 0.5 mM to 1.5 mM, and particularly about 0.67 mM.

The Examples that follow are illustrative of specific embodiments of the disclosure, and various uses thereof. They set forth for explanatory purposes only, and are not to be taken as limiting the disclosure.

EXAMPLE 1

Test for Sialyltransferase Enzymatic Activity

Asialofetuin (desialylated fetuin, Roche Applied Science) was used as acceptor and CMP-9-fluoro-NANA (CMP-9-fluoresceinyl-NeuAc) was used as donor substrate (Brossmer, R. & Gross H. J. (1994) Meth. Enzymol. 247, 177-193). Enzymatic activity was determined by measuring the transfer of sialic acid from the donor compound to asialofetuin. The reaction mix (35 mM MES, pH 6.0, 0,035% Triton X-100, 0.07% BSA) contained 2.5 µg of enzyme sample, 5

µL asialofetuin (20 mg/ml) and 2 µL CMP-9-fluoro-NANA (1.0 mg/ml) in a total volume of 51 µL. The reaction mix was incubated at 37° C. for 30 minutes. The reaction was stopped by the addition of 10 µL of the inhibitor CTP (10 mM). The reaction mix was loaded onto a PD10 desalting column equilibrated with 0.1 M Tris/HCl, pH 8.5. Fetuin was eluted from the column using the equilibration buffer. The fractions size was 1 mL. The concentration of formed fetuin was determined using a fluorescence spectrophotometer. Excitation wave length was 490 nm, emission was measured at 520 nm. Enzymatic activity was expressed as RFU (relative fluorescence unit). 10 000 RFU/µg is equivalent to a specific activity of 0.0839 nmol/µg×min.

EXAMPLE 2

SDS Gel Electrophoresis

Analytical SDS gel electrophoresis was carried out using NuPAGE gels (4-12%, Invitrogen). Samples (36 µl) were diluted with 12 µl NuPAGE LDS sample buffer (Invitrogen) and incubated for 2 min at 85° C. Aliquots, typically containing 5 µg protein were loaded on the gel. The gels were stained using SimplyBlue SafeStain (Invitrogen).

EXAMPLE 3

N-Terminal Sequencing by Edman Degradation

The N-terminal sequences of expressed variants of human ST6Gal-I were analyzed by Edman degradation using reagents and devices obtained from Life Technologies. Preparation of the samples was done as described in the instruction manual of the ProSorb Sample Preparation cartridges (catalog number 401950) and the ProBlott Mini PK/10 membranes (catalog number 01194). For sequencing the Procise Protein Sequencing Platform was used.

EXAMPLE 4

Mass Spectrometry

The molecular masses of variants of human ST6Gal-I expressed in HEK cells were analyzed in mass spectroscopy. Therefore, the glycosylated and deglycosylated forms of human ST6Gal-I were prepared and analyzed using Micromass Q-Tof Ultima and Synapt G2 HDMS devices (Waters UK) and MassLynx V 4.1 software.

EXAMPLE 5

Mass Spectrometry of Glycosylated Human ST6Gal-I Enzymes

For mass spectrometry measurement the samples were buffered in electrospray medium (20% acetonitrile+1% formic acid). The buffer exchange was performed with illustra™ MicroSpin™ G-25 columns (GE-Healthcare). 20 µg sialyltransferase variant with a concentration of 1 mg/ml was applied to the pre-equilibrated column and eluated by centrifugation. The resulting eluate was analyzed by electrospray ionization mass spectrometry.

EXAMPLE 6

Mass Spectrometry of Deglycosylated Human ST6Gal-I Enzymes

For deglycosylation samples of the sialyltransferase were denatured and reduced. To 100 µg sialyltransferase 45 µL denaturing buffer (6 M guanidinium hydrochloride) and 13 µL TCEP (0.1 mM, diluted in denaturing buffer) were added. Further the appropriate volume of ultrapure water was added, so that the overall concentration of guanidinium hydrochloride was about 4 M. After incubation of the sample for 1 hour at 37° C. the buffer was changed using a Bio-SpinR 6 Tris column (Bio Rad), which was pre-equilibrated with ultrapure water. The whole sample was applied onto the column and eluted by centrifugation. To the resulting eluate 5.5 µl of 0.1 U/µl solution of PNGase F was added and incubated at 37° C. over night. Afterwards the samples were adjusted to 30% ACN and 1% FA and analyzed by electrospray ionization mass spectrometry.

EXAMPLE 7

Cloning of pM1MT Expression Constructs for Transient Gene Expression (TGE) in Mammalian Host Cells Truncated variant Δ89 of human ST6Gal-I was cloned for transient expression using an Erythropoietin signal peptide sequence (Epo) and a peptide spacer of two amino acids ("AP"). For the Epo-AP-Δ89 hST6Gal-I construct codon-optimized cDNAs were synthesized, see SEQ ID NO:3. Instead of the natural leader sequences and the N-terminal protein sequences, the hST6Gal-I coding region harbors the Erythropoietin signal sequence plus AP linker sequence in order to ensure correct processing of expressed polypeptides by the secretion machinery of the host cell line. In addition, the expression cassettes features SalI and BamHI restriction sites for cloning into the multiple cloning site of the predigested pM1MT vector fragment (Roche Applied Science). Expression of the ST6Gal-I coding sequence is therefore under control of a human cytomegalovirus (CMV) immediate-early enhancer/promoter region, followed by an "intron A" for regulated expression, and a BGH polyadenylation signal.

Expression of the Epo-AP-Δ89 hST6Gal-I conctruct in HEK cells, and secretion of Δ89 hST6Gal-I protein into cell supernatant was performed as described in Example 8.

EXAMPLE 8

Transformation HEK Cells and Transient Expression and Secretion

Transient gene expression (TGE) by transfection of plasmid DNA is a rapid strategy to produce proteins in mammalian cell culture. For high-level expression of recombinant human proteins a TGE platform based on a suspension-adapted human embryonic kidney (HEK) 293 cell line was used. Cells were cultured in shaker flasks at 37° C. under serum-free medium conditions. The cells were transfected at approx. $2\times10^6$ vc/ml with the pM1MT expression plasmids (0.5 to 1 mg/L cell culture) complexed by the 293-Free™ (Merck) transfection reagent according to the manufacturer's guidelines. Three hours post-transfection, valproic acid, a HDAC inhibitor, was added (final conc. 4 mM) in order to boost the expression (Backliwal et al. (2008), Nucleic Acids Research 36, e96). Each day, the culture was supplemented with 6% (v/v) of a soybean peptone hydrolysate-based feed. The culture supernatant was collected at day 7 post-transfection by centrifugation.

EXAMPLE 9

Purification of the Δ89 N-Terminal Truncation Variant of Human ST6Gal-I (Δ89 hST6Gal-I) from Supernatants of Transformed HEK Cells HEK cells were transformed as described in Example 8. The expression construct was prepared as described in Example 7. The particular hST6Gal-I coding sequence was a nucleotide sequence encoding the Δ89 hST6Gal-I N-terminal truncation variant, the expressed construct therefore was Epo-AP-Δ89-hST6Gal-I.

From supernatants of HEK cell fermentations the variant Epo-AP-Δ89 hST6Gal-I was purified using a simplified purification protocol. In a first step, 0.1 liter of culture supernatant was filtrated (0.2 μm), the solution was dialysed against buffer A (20 mM potassium phosphate, pH 6.5). The dialysate was loaded onto a S-Sepharose™ ff (Fast Flow) column (1.6 cm×2 cm) equilibrated with buffer A. After washing with 100 mL buffer A, the enzyme was eluted with a linear gradient of 10 mL buffer A and 10 mL of buffer A+200 mM NaCl, followed by a wash step using 48 mL of buffer A+200 mM NaCl. Fractions (4 mL) were analysed by an analytical SDS gel electrophoresis.

Fractions containing the enzyme were pooled and dialyzed against buffer B (50 mM MES, pH 6.0). The dialyzed pool was loaded onto a Heparin Sepharose ff column (0.5 cm×5 cm) equilibrated with buffer B and eluted using buffer B+200 m M NaCl. Fractions (1 ml) containing the enzyme were pooled and dialyzed against buffer B. Protein concentrations were determined at 280 nm (E280 nm [1 mg/ml] =1.931). Mass spectrometry analysis of the enzyme showed that the construct of Epo-AP-Δ89 hST6Gal-I was secreted without the N-terminal amino acids AP. This surprising finding indicated an unusual cleavage of the expressed protein by the signal peptidase while removing the Epo portion. For the recombinant human Δ89 hST6Gal-I a specific activity of >1100 RFU/μg was determined FIG. 1 shows the results of a SDS-PAGE of purified recombinant Δ89 hST6Gal-I variant from HEK cells.

EXAMPLE 10

Sialylation of Humanized Monoclonal Antibody (MAB) Using Δ89 hST6Gal-I

A highly galactosylated humanized monoclonal antibody IgG4 MAB<IL-1R>(WO 2005/023872) was used in sialylation experiments. The reaction mixture contained MAB<IL-1R>(300 μg in 55 μl 35 mM sodium actetate/Tris buffer pH 7.0), the donor substrate CMP-NANA (150 μg in 50 μl water) and sialyltransferase (30 μg Δ89 hST6Gal-I in 20 mM potassium phosphate, 0.1 M NaCl, pH 6.5). The samples were incubated at 37° C. for a defined time. To stop the reaction the samples were frozen at −20° C. For mass analysis 100 μl denaturing buffer (6 M guanidinium chloride) and 30 μl TCEP (0.1 mM, diluted in denaturing buffer) were added to the samples and the samples were incubated at 37° C. for 1 h. The sample were buffered in electrospray-medium (20% ACN, 1% FA) using pre-equilibrated illustra™ Nap5-Columns (GE-Healthcare). Samples were analyzed by electrospray ionization mass spectrometry and the content of G2+0SA, G2+1SA and G2+2SA N-glycans was determined. A Micromass Q-Tof Ultima and a Synapt G2 HDMS device (Waters UK) were used, the software used was MassLynx V 4.1. To determine the kinetics of the sialylation the reaction was incubated up to 72 h. FIG. 2 shows the relative amounts of differently sialylated target proteins obtained after different time points during the incubation period.

The content of G2+0SA, G2+1SA and G2+2SA was determined by mass spectrometry. For the variant Δ89 hST6Gal-I already after 2 hours of incubation a high content (88%) of the bi-sialylated form G2+2SA was obtained, see FIG. 2. The data also show that the content of G2+0SA and G2+1SA again increased over time due to the intrinsic sialidase (neuraminidase) activity of Δ89 hST6Gal-I. After an incubation of 48 h a G2+1SA content of 71% was obtained. Therefore, it is possible to obtain preferably mono- or bi-sialylated forms of the immunoglobulin by using only one single enzyme and simply varying the incubation times.

Figure 3A:
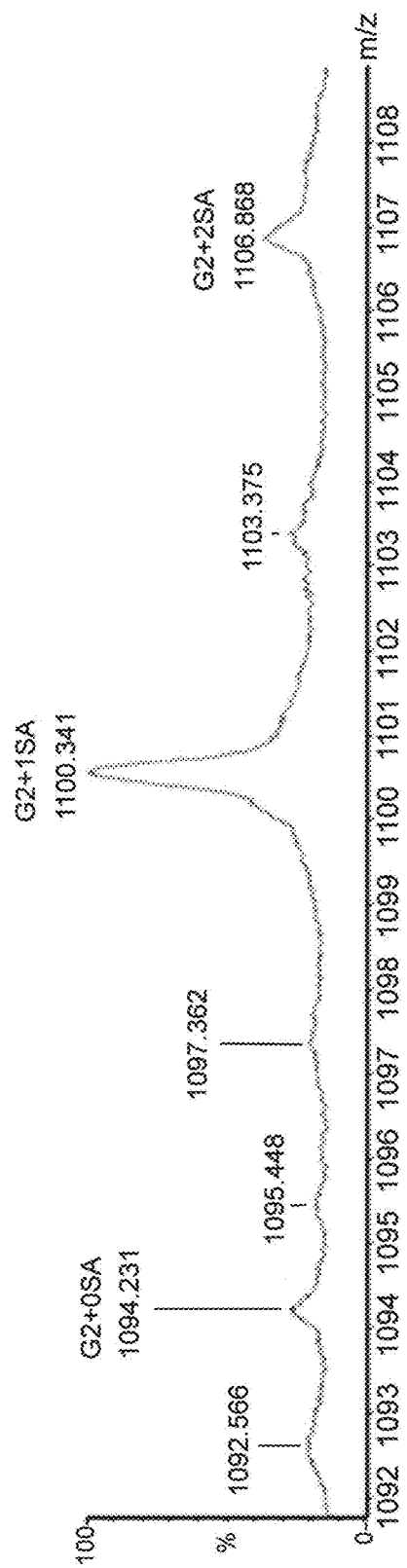
FIG. 3A Kinetics of formation of G2+2SA and G2+1SA, catalyzed by recombinant Δ89 hST6Gal-I, as shown by mass spectra taken as a basis for determination of the relative content of the different sialylated target molecule species.
Figure 3B:
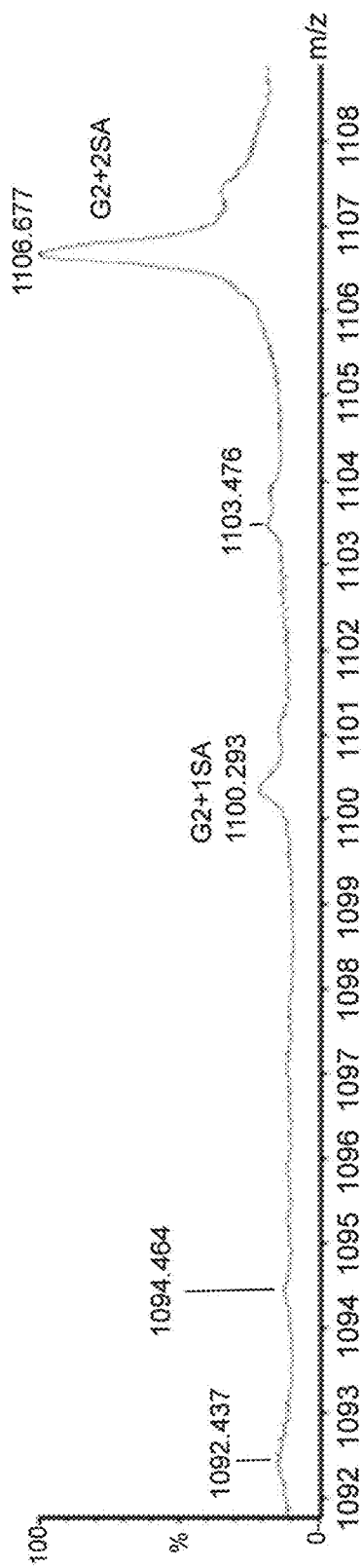
FIG. 3B Kinetics of formation of G2+2SA and G2+1SA, catalyzed by recombinant Δ89 hST6Gal-I, as shown by mass spectra taken as a basis for determination of the relative content of the different sialylated target molecule species.
Figure 3C:
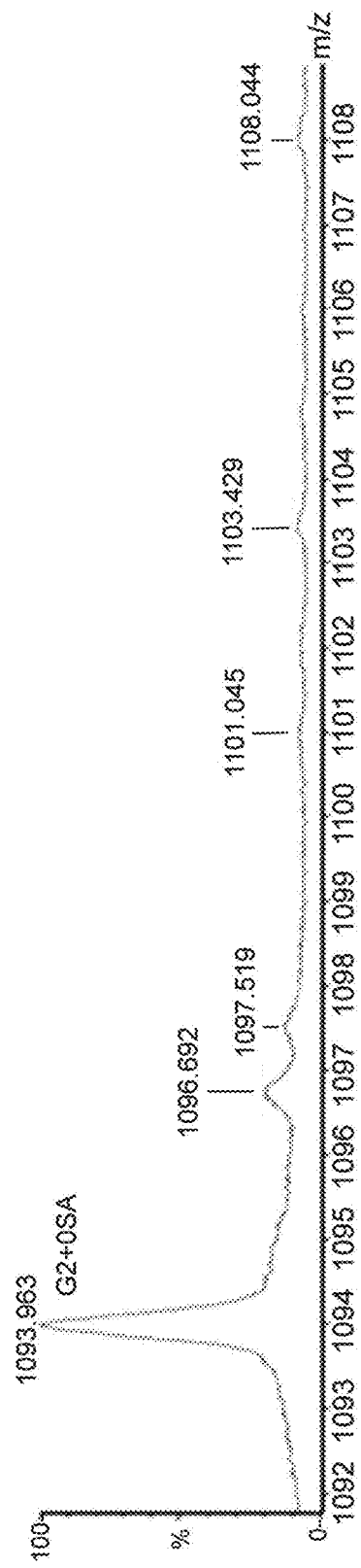
FIG. 3C Kinetics of formation of G2+2SA and G2+1SA, catalyzed by recombinant Δ89 hST6Gal-I, as shown by mass spectra taken as a basis for determination of the relative content of the different sialylated target molecule species.

FIG. 3 shows the spectra obtained by mass spectrometric analysis of different samples of MAB <IL-1R>. Samples were taken at time point t=0 (lower panel), time point t=8 h (middle panel) and time point t=48 h (upper panel). The mass over charge (m/z) signals of one charge state in the mass spectrum of the IgG molecule with G2+0SA, G2+1SA and G2+2SA glycans are depicted. The relative intensities of the different sialylated species are derived from these signals. Corresponding to FIG. 2, at t=0 h G2+0SA is the major glycan species. At t=8 h the signal for G2+2SA is the dominant form whereas at t=48 h, G2+1SA is the most abundant species. For the determined numerical values see FIG. 2.

EXAMPLE 11

Inhibition of Sialidase Activity of Δ89 hST6Gal-I

Figure 4:
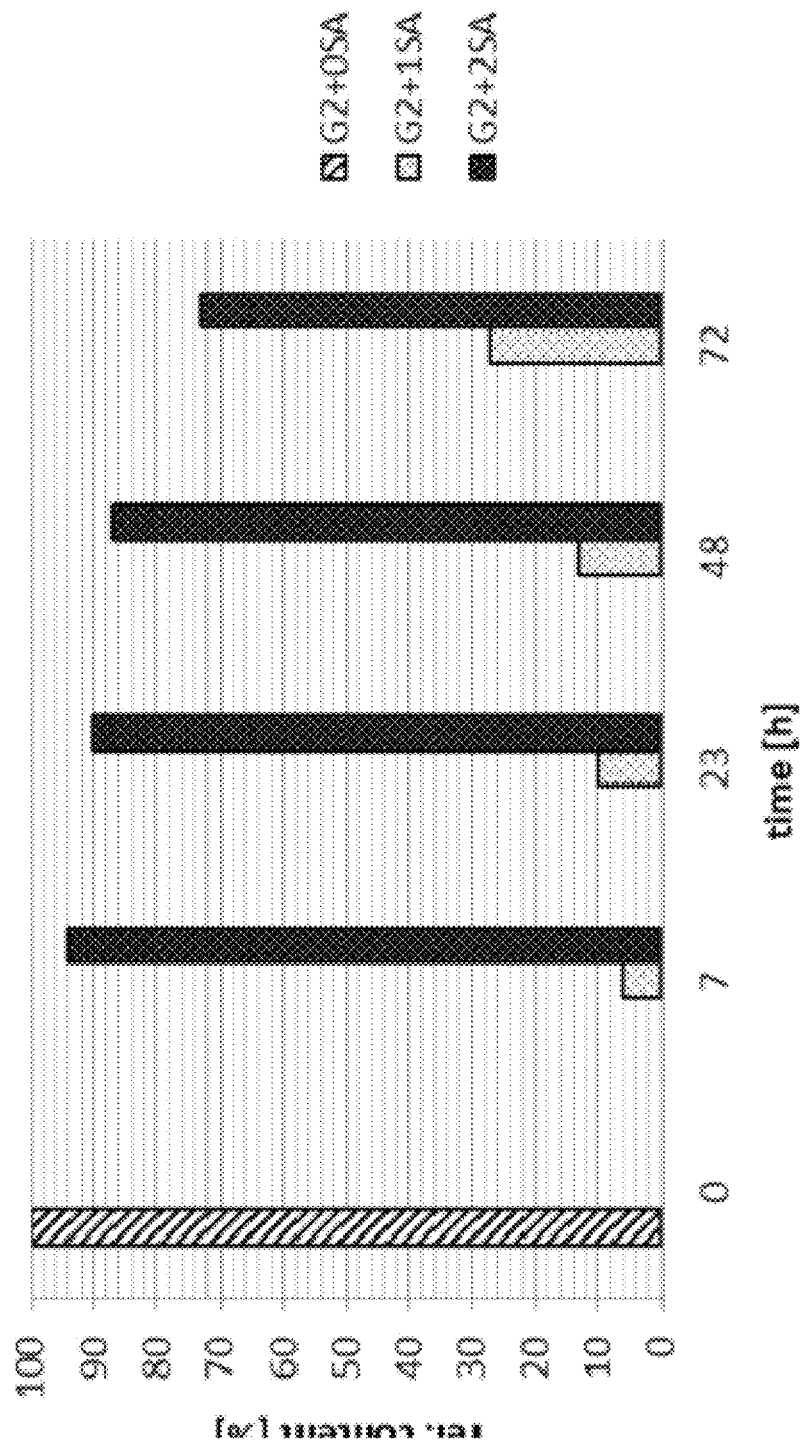
FIG. 4 Inhibition of sialidase activity of recombinant Δ89 hST6Gal-I by CTP. The relative content of glycan with terminal galactose residues (G2+0SA, "asialo"), mono-sialylated glycan (G2+1SA) and bi-sialylated glycan (G2+2SA) is shown.

The compound cytidine triphosphate (CTP) is a potent inhibitor of sialyltransferases (Scudder P R & Chantler E N B B A 660 (1981) 136-141). To demonstrate that the sialidase activity is an intrinsic activity of Δ89 hST6Gal-I, inhibition experiments were performed. In the first phase of the experiment the sialylation of MAB <IL-1R> by Δ89 hST6Gal-I was performed to achieve a high content of G2+2SA (see Example 10). After 7 h of incubation the G2+2SA content was 94%. Subsequently, CTP was added to inhibit the sialidase activity of Δ89 hST6Gal-I (final concentration of CTP: 0.67 mM). At different times samples were taken and the content of G2+0SA, G2+1SA and G2+2SA was determined by mass spectrometry. The results are shown in FIG. 4. Compared to inhibitor-free conditions shown in FIG. 2 the degradation of G2+2SA caused by the sialidase activity was significantly reduced. After 72 h of incubation 73% of G2+2SA were still present. The inhibition of the sialidase activity by a known inhibitor of sialyltransferase activity strongly indicates that both activities are located in the same active center of Δ89 hST6Gal-I.

The invention claimed is:

1. A method of producing in vitro a sialylated target molecule with a controlled quantity of sialyl residues, the method comprising the steps of
    (a) providing a glycosylated target molecule in an aqueous solution and under conditions permitting glycosyltransferase enzymatic activity, the target molecule being selected from a glycoprotein and a glycolipid, the target molecule comprising a plurality of antennae, at least two of the antennae each having as terminal structure a β-D-galactosyl-1,4-N-acetyl-β-D-glucosamine moiety with a hydroxyl group at the C6 position in the galactosyl residue;
    (b) forming one or more terminal antennal N-acetylneuraminyl-α2,6-β-D-galactosyl-1,4-N-acetyl-β-D-glucosamine residue(s) [=α2,6 sialylated terminal antennal residue(s)] by incubating the target molecule of step (a) for a first pre-determined time with N-terminally truncated human β-galactoside-α-2,6-sialyltransferase I having the amino acid sequence of SEQ ID NO:2 and in the presence of cytidine-5'-monophospho-N-acetylneuraminic acid, or a functional equivalent thereof, as donor compound thereby providing a sialylated target molecule;
    (c) hydrolyzing the α2,6 glycosidic bond in one or more terminal antennal N-acetylneuraminyl-α2,6-β-D-galactosyl-1,4-N-acetyl-β-D-glucosamine residues by incubating the sialylated target molecule of step (b) for a second pre-determined time with the N-terminally truncated human β-galactoside-α-2,6-sialyltransferase I having the amino acid sequence of SEQ ID NO:2;
thereby producing in vitro the sialylated target molecule with a controlled quantity of sialyl residues.

2. The method according to claim 1, wherein between the steps (b) and (c) sialylation of the target molecule is determined quantitatively.

3. The method according to claim 1 wherein after step (c) sialylation of the target molecule is determined quantitatively.

4. The method according to claim 1, wherein steps (a), (b) and (c) are performed continuously in the same vessel.

5. The method according to claim 1, wherein the target molecule is a purified immunoglobulin molecule of the IgG class, particularly a monoclonal antibody of an immunoglobulin class selected from IgG1, IgG2, IgG3 and IgG4.

6. The method according to claim 5, wherein steps (a), (b) and (c) are performed continuously in the same vessel with a measured amount of target molecules, wherein step (b) is performed for 0 h to about 24 h and subsequent step (c) is performed for 0 h, and wherein the relative amount of bi-sialylated target molecules is about 35% to about 90%.

7. The method according to claim 5, wherein steps (a), (b) and (c) are performed continuously in the same vessel with a measured amount of target molecules, wherein step (b) is performed for 24 h and subsequent step (c) is performed for 0 h to about 72 h or longer, and wherein the relative amount of mono-sialylated target molecules is about 60% to about 75%.

8. The method according to claim 6, wherein the weight-by-weight [w/w] ratio of target (immunoglobulin) molecules : human β-galactoside-α-2,6-sialyltransferase I molecules is 10:1, wherein each has a relative purity of 80% or higher.

* * * * *

SEQUENCE LISTING

```
<160> NUMBER OF SEQ ID NOS: 4

<210> SEQ ID NO 1
<211> LENGTH: 406
<212> TYPE: PRT
<213> ORGANISM: Homo sapiens
<220> FEATURE:
```

<221> NAME/KEY: MISC_FEATURE
<223> OTHER INFORMATION: hST6-Gal-I WT polypeptide

<400> SEQUENCE: 1

```
Met Ile His Thr Asn Leu Lys Lys Phe Ser Cys Cys Val Leu Val
1               5                   10                  15

Phe Leu Leu Phe Ala Val Ile Cys Val Trp Lys Glu Lys Lys Gly
                20                  25                  30

Ser Tyr Tyr Asp Ser Phe Lys Leu Gln Thr Lys Glu Phe Gln Val Leu
            35                  40                  45

Lys Ser Leu Gly Lys Leu Ala Met Gly Ser Asp Ser Gln Ser Val Ser
    50                  55                  60

Ser Ser Ser Thr Gln Asp Pro His Arg Gly Arg Gln Thr Leu Gly Ser
65                  70                  75                  80

Leu Arg Gly Leu Ala Lys Ala Lys Pro Glu Ala Ser Phe Gln Val Trp
                85                  90                  95

Asn Lys Asp Ser Ser Ser Lys Asn Leu Ile Pro Arg Leu Gln Lys Ile
                100                 105                 110

Trp Lys Asn Tyr Leu Ser Met Asn Lys Tyr Lys Val Ser Tyr Lys Gly
            115                 120                 125

Pro Gly Pro Gly Ile Lys Phe Ser Ala Glu Ala Leu Arg Cys His Leu
    130                 135                 140

Arg Asp His Val Asn Val Ser Met Val Glu Val Thr Asp Phe Pro Phe
145                 150                 155                 160

Asn Thr Ser Glu Trp Glu Gly Tyr Leu Pro Lys Glu Ser Ile Arg Thr
                165                 170                 175

Lys Ala Gly Pro Trp Gly Arg Cys Ala Val Val Ser Ser Ala Gly Ser
            180                 185                 190

Leu Lys Ser Ser Gln Leu Gly Arg Glu Ile Asp Asp His Asp Ala Val
    195                 200                 205

Leu Arg Phe Asn Gly Ala Pro Thr Ala Asn Phe Gln Gln Asp Val Gly
210                 215                 220

Thr Lys Thr Thr Ile Arg Leu Met Asn Ser Gln Leu Val Thr Thr Glu
225                 230                 235                 240

Lys Arg Phe Leu Lys Asp Ser Leu Tyr Asn Glu Gly Ile Leu Ile Val
                245                 250                 255

Trp Asp Pro Ser Val Tyr His Ser Asp Ile Pro Lys Trp Tyr Gln Asn
            260                 265                 270

Pro Asp Tyr Asn Phe Phe Asn Asn Tyr Lys Thr Tyr Arg Lys Leu His
    275                 280                 285

Pro Asn Gln Pro Phe Tyr Ile Leu Lys Pro Gln Met Pro Trp Glu Leu
290                 295                 300

Trp Asp Ile Leu Gln Glu Ile Ser Pro Glu Glu Ile Gln Pro Asn Pro
305                 310                 315                 320

Pro Ser Ser Gly Met Leu Gly Ile Ile Ile Met Met Thr Leu Cys Asp
                325                 330                 335

Gln Val Asp Ile Tyr Glu Phe Leu Pro Ser Lys Arg Lys Thr Asp Val
            340                 345                 350

Cys Tyr Tyr Tyr Gln Lys Phe Phe Asp Ser Ala Cys Thr Met Gly Ala
    355                 360                 365

Tyr His Pro Leu Leu Tyr Glu Lys Asn Leu Val Lys His Leu Asn Gln
370                 375                 380

Gly Thr Asp Glu Asp Ile Tyr Leu Leu Gly Lys Ala Thr Leu Pro Gly
385                 390                 395                 400
```

Phe Arg Thr Ile His Cys
            405

<210> SEQ ID NO 2
<211> LENGTH: 317
<212> TYPE: PRT
<213> ORGANISM: Artificial Sequence
<220> FEATURE:
<223> OTHER INFORMATION: delta89 truncation variant of hST6Gal-I

<400> SEQUENCE: 2

Glu Ala Ser Phe Gln Val Trp Asn Lys Asp Ser Ser Lys Asn Leu
1               5                   10                  15

Ile Pro Arg Leu Gln Lys Ile Trp Lys Asn Tyr Leu Ser Met Asn Lys
            20                  25                  30

Tyr Lys Val Ser Tyr Lys Gly Pro Gly Pro Gly Ile Lys Phe Ser Ala
        35                  40                  45

Glu Ala Leu Arg Cys His Leu Arg Asp His Val Asn Val Ser Met Val
    50                  55                  60

Glu Val Thr Asp Phe Pro Phe Asn Thr Ser Glu Trp Glu Gly Tyr Leu
65                  70                  75                  80

Pro Lys Glu Ser Ile Arg Thr Lys Ala Gly Pro Trp Gly Arg Cys Ala
                85                  90                  95

Val Val Ser Ser Ala Gly Ser Leu Lys Ser Ser Gln Leu Gly Arg Glu
            100                 105                 110

Ile Asp Asp His Asp Ala Val Leu Arg Phe Asn Gly Ala Pro Thr Ala
        115                 120                 125

Asn Phe Gln Gln Asp Val Gly Thr Lys Thr Thr Ile Arg Leu Met Asn
    130                 135                 140

Ser Gln Leu Val Thr Thr Glu Lys Arg Phe Leu Lys Asp Ser Leu Tyr
145                 150                 155                 160

Asn Glu Gly Ile Leu Ile Val Trp Asp Pro Ser Val Tyr His Ser Asp
                165                 170                 175

Ile Pro Lys Trp Tyr Gln Asn Pro Asp Tyr Asn Phe Phe Asn Asn Tyr
            180                 185                 190

Lys Thr Tyr Arg Lys Leu His Pro Asn Gln Pro Phe Tyr Ile Leu Lys
        195                 200                 205

Pro Gln Met Pro Trp Glu Leu Trp Asp Ile Leu Gln Glu Ile Ser Pro
    210                 215                 220

Glu Glu Ile Gln Pro Asn Pro Pro Ser Ser Gly Met Leu Gly Ile Ile
225                 230                 235                 240

Ile Met Met Thr Leu Cys Asp Gln Val Asp Ile Tyr Glu Phe Leu Pro
                245                 250                 255

Ser Lys Arg Lys Thr Asp Val Cys Tyr Tyr Tyr Gln Lys Phe Phe Asp
            260                 265                 270

Ser Ala Cys Thr Met Gly Ala Tyr His Pro Leu Leu Tyr Glu Lys Asn
        275                 280                 285

Leu Val Lys His Leu Asn Gln Gly Thr Asp Glu Asp Ile Tyr Leu Leu
    290                 295                 300

Gly Lys Ala Thr Leu Pro Gly Phe Arg Thr Ile His Cys
305                 310                 315

<210> SEQ ID NO 3
<211> LENGTH: 1054
<212> TYPE: DNA
<213> ORGANISM: Artificial Sequence

```
<220> FEATURE:
<223> OTHER INFORMATION: Expression construct Epo-AP-delta89 ST6
      (90-406)
<220> FEATURE:
<221> NAME/KEY: misc_recomb
<222> LOCATION: (1)..(6)
<223> OTHER INFORMATION: Sal-I restriction site
<220> FEATURE:
<221> NAME/KEY: CDS
<222> LOCATION: (8)..(1048)
<223> OTHER INFORMATION: nucleic acid sequence encoding a fusion
      polypeptide of delta89 hST6-Gal-I, N-terminally fused to the Epo
      leader peptide and containing an "AP" joining sequence
<220> FEATURE:
<221> NAME/KEY: misc_feature
<222> LOCATION: (95)..(1048)
<223> OTHER INFORMATION: portion ot the nucleic acid sequence encoding
      the delta89 hST6-Gal-I portion of the fusion polypeptide
<220> FEATURE:
<221> NAME/KEY: misc_recomb
<222> LOCATION: (1049)..(1054)
<223> OTHER INFORMATION: BamH-I restriction site

<400> SEQUENCE: 3
```

| | | | | | | | | | | | | | | |
|---|---|---|---|---|---|---|---|---|---|---|---|---|---|---|
| gtcgacc | atg | ggc | gtg | cac | gaa | tgt | cct | gcc | tgg | ctg | tgg | ctg | ctg | 49 |
| | Met | Gly | Val | His | Glu | Cys | Pro | Ala | Trp | Leu | Trp | Leu | Leu | |
| | 1 | | | 5 | | | | | 10 | | | | | |

```
agc ctg ctg tct ctg cct ctg gga ctg cct gtg ctg ggc gcc cct gaa      97
Ser Leu Leu Ser Leu Pro Leu Gly Leu Pro Val Leu Gly Ala Pro Glu
 15              20              25              30 gcc tct ttc cag gtg tgg aac aag gac agc agc tcc aag aac ctg atc     145
Ala Ser Phe Gln Val Trp Asn Lys Asp Ser Ser Ser Lys Asn Leu Ile
             35              40              45 ccc cgg ctg cag aag atc tgg aag aac tac ctg agc atg aac aag tac     193
Pro Arg Leu Gln Lys Ile Trp Lys Asn Tyr Leu Ser Met Asn Lys Tyr
         50              55              60 aag gtg tcc tac aag ggc cct ggc cct ggc atc aag ttt agc gcc gag     241
Lys Val Ser Tyr Lys Gly Pro Gly Pro Gly Ile Lys Phe Ser Ala Glu
             65              70              75 gcc ctg aga tgc cac ctg agg gat cac gtg aac gtg tcc atg gtg gaa     289
Ala Leu Arg Cys His Leu Arg Asp His Val Asn Val Ser Met Val Glu
 80              85              90 gtg acc gac ttc cca ttc aac acc agc gag tgg gag ggc tac ctg ccc     337
Val Thr Asp Phe Pro Phe Asn Thr Ser Glu Trp Glu Gly Tyr Leu Pro
 95             100             105             110 aaa gag agc atc cgg acc aaa gcc ggc cct tgg gga aga tgt gcc gtg     385
Lys Glu Ser Ile Arg Thr Lys Ala Gly Pro Trp Gly Arg Cys Ala Val
             115             120             125 gtg tct agc gcc ggc agc ctg aag agt agc cag ctg ggc aga gag atc     433
Val Ser Ser Ala Gly Ser Leu Lys Ser Ser Gln Leu Gly Arg Glu Ile
         130             135             140 gac gac cac gac gcc gtg ctg cgg ttc aat ggc gct ccc acc gcc aac     481
Asp Asp His Asp Ala Val Leu Arg Phe Asn Gly Ala Pro Thr Ala Asn
             145             150             155 ttc cag cag gac gtg ggc acc aag acc acc atc cgg ctg atg aac tcc     529
Phe Gln Gln Asp Val Gly Thr Lys Thr Thr Ile Arg Leu Met Asn Ser
     160             165             170 cag ctc gtg aca acc gag aag cgg ttc ctg aag gac agc ctg tac aac     577
Gln Leu Val Thr Thr Glu Lys Arg Phe Leu Lys Asp Ser Leu Tyr Asn
 175             180             185             190 gag ggc atc ctg atc gtg tgg gac ccc agc gtg tac cac agc gac atc     625
Glu Gly Ile Leu Ile Val Trp Asp Pro Ser Val Tyr His Ser Asp Ile
             195             200             205 ccc aag tgg tat cag aac ccc gac tac aac ttc ttc aac aac tac aag     673
Pro Lys Trp Tyr Gln Asn Pro Asp Tyr Asn Phe Phe Asn Asn Tyr Lys
```

```
                   210                 215                 220
acc tac cgg aag ctg cac ccc aac cag ccc ttc tac atc ctg aag ccc        721
Thr Tyr Arg Lys Leu His Pro Asn Gln Pro Phe Tyr Ile Leu Lys Pro
            225                 230                 235 cag atg ccc tgg gag ctg tgg gac att ctg cag gaa atc agc ccc gaa        769
Gln Met Pro Trp Glu Leu Trp Asp Ile Leu Gln Glu Ile Ser Pro Glu
240                 245                 250 gag atc cag ccc aac ccc cct agc tct ggc atg ctg ggc atc att atc        817
Glu Ile Gln Pro Asn Pro Pro Ser Ser Gly Met Leu Gly Ile Ile Ile
255                 260                 265                 270 atg atg acc ctg tgc gac cag gtg gac atc tac gag ttt ctg ccc tcc        865
Met Met Thr Leu Cys Asp Gln Val Asp Ile Tyr Glu Phe Leu Pro Ser
                275                 280                 285 aag aga aag acc gac gtg tgc tac tac tac cag aag ttc ttc gac agc        913
Lys Arg Lys Thr Asp Val Cys Tyr Tyr Tyr Gln Lys Phe Phe Asp Ser
            290                 295                 300 gcc tgc acc atg gga gcc tac cac cct ctg ctg tac gag aag aac ctc        961
Ala Cys Thr Met Gly Ala Tyr His Pro Leu Leu Tyr Glu Lys Asn Leu
        305                 310                 315 gtg aag cac ctg aac cag ggc acc gac gag gat atc tac ctg ctg ggc       1009
Val Lys His Leu Asn Gln Gly Thr Asp Glu Asp Ile Tyr Leu Leu Gly
320                 325                 330 aag gcc acc ctg ccc ggc ttc aga acc atc cac tgc tga ggatcc            1054
Lys Ala Thr Leu Pro Gly Phe Arg Thr Ile His Cys
335                 340                 345

<210> SEQ ID NO 4
<211> LENGTH: 346
<212> TYPE: PRT
<213> ORGANISM: Artificial Sequence
<220> FEATURE:
<223> OTHER INFORMATION: Synthetic Construct

<400> SEQUENCE: 4

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Glu Ala Ser
            20                  25                  30

Phe Gln Val Trp Asn Lys Asp Ser Ser Lys Asn Leu Ile Pro Arg
        35                  40                  45

Leu Gln Lys Ile Trp Lys Asn Tyr Leu Ser Met Asn Lys Tyr Lys Val
    50                  55                  60

Ser Tyr Lys Gly Pro Gly Pro Gly Ile Lys Phe Ser Ala Glu Ala Leu
65                  70                  75                  80

Arg Cys His Leu Arg Asp His Val Asn Val Ser Met Val Glu Val Thr
                85                  90                  95

Asp Phe Pro Phe Asn Thr Ser Glu Trp Glu Gly Tyr Leu Pro Lys Glu
            100                 105                 110

Ser Ile Arg Thr Lys Ala Gly Pro Trp Gly Arg Cys Ala Val Val Ser
        115                 120                 125

Ser Ala Gly Ser Leu Lys Ser Ser Gln Leu Gly Arg Glu Ile Asp Asp
    130                 135                 140

His Asp Ala Val Leu Arg Phe Asn Gly Ala Pro Thr Ala Asn Phe Gln
145                 150                 155                 160

Gln Asp Val Gly Thr Lys Thr Thr Ile Arg Leu Met Asn Ser Gln Leu
                165                 170                 175

Val Thr Thr Glu Lys Arg Phe Leu Lys Asp Ser Leu Tyr Asn Glu Gly
            180                 185                 190
```

```
Ile Leu Ile Val Trp Asp Pro Ser Val Tyr His Ser Asp Ile Pro Lys
        195             200             205
Trp Tyr Gln Asn Pro Asp Tyr Asn Phe Phe Asn Asn Tyr Lys Thr Tyr
    210             215             220
Arg Lys Leu His Pro Asn Gln Pro Phe Tyr Ile Leu Lys Pro Gln Met
225             230             235             240
Pro Trp Glu Leu Trp Asp Ile Leu Gln Glu Ile Ser Pro Glu Glu Ile
            245             250             255
Gln Pro Asn Pro Pro Ser Ser Gly Met Leu Gly Ile Ile Ile Met Met
                260             265             270
Thr Leu Cys Asp Gln Val Asp Ile Tyr Glu Phe Leu Pro Ser Lys Arg
            275             280             285
Lys Thr Asp Val Cys Tyr Tyr Tyr Gln Lys Phe Phe Asp Ser Ala Cys
        290             295             300
Thr Met Gly Ala Tyr His Pro Leu Leu Tyr Glu Lys Asn Leu Val Lys
305             310             315             320
His Leu Asn Gln Gly Thr Asp Glu Asp Ile Tyr Leu Leu Gly Lys Ala
                325             330             335
Thr Leu Pro Gly Phe Arg Thr Ile His Cys
            340             345
```